(12) United States Patent
Torigoe et al.

(10) Patent No.: US 6,559,298 B1
(45) Date of Patent: May 6, 2003

(54) POLYPEPTIDES THAT BIND INTERLEUKIN-18 (IL-18)

(75) Inventors: Kakuji Torigoe, Okayama (JP); Takanori Okura, Okayama (JP); Masashi Kurimoto, Okayama (JP)

(73) Assignee: Kabushiki Kaisha Hayashibara Seibutsu Kagaku Kenkyujo (JP)

( * ) Notice: Subject to any disclaimer, the term of this patent is extended or adjusted under 35 U.S.C. 154(b) by 0 days.

(21) Appl. No.: 09/556,972

(22) Filed: Apr. 24, 2000

Related U.S. Application Data

(62) Division of application No. 08/996,338, filed on Dec. 22, 1997, now Pat. No. 6,087,116.

(30) Foreign Application Priority Data

| Mar. 19, 1997 | (JP) | 9/74697 |
| Jul. 28, 1997 | (JP) | 9/215488 |
| Oct. 9, 1997 | (JP) | 9/291837 |

(51) Int. Cl.⁷ ................ C07H 21/04; C12N 15/00; C12N 15/63; G01N 30/00
(52) U.S. Cl. ............... 536/23.5; 435/69.1; 435/7.1; 435/70.1; 435/325; 435/172.3; 435/252.3; 435/320.1; 435/69.52; 536/24.3; 536/23.1; 530/300; 530/350; 530/351; 530/412; 530/413
(58) Field of Search ............... 435/69.1, 7.1, 435/70.1, 325, 172.3, 252.3, 320.1, 69.52; 536/24.3, 23.1, 23.5; 530/300, 350, 351, 412, 413

(56) References Cited

U.S. PATENT DOCUMENTS 5,776,731 A   7/1998   Parnet et al. ............... 435/69.1

FOREIGN PATENT DOCUMENTS

| EP | 0658627 | 6/1994 |
| EP | 0712931 | 5/1995 |
| EP | 0692536 | 1/1996 |
| JP | 7163368 | 6/1995 |
| JP | 827189 | 1/1996 |
| JP | 8193098 | 7/1996 |
| WO | 9731010 | 8/1997 |

OTHER PUBLICATIONS

H. Okamura et al., "Cloning of a new cytokine that induces IFN–y production by T cells", Nature, vol. 378, No. 6552, pp 88–91, Nov. 2, 1995

S. Ushio et al., "Cloning of the cDNA for human IFN–y inducing factor, expression in *escherichia coli*, and studies on the biologic activities of the protein", The Journal of Immunology, vol. 156, pp. 4274–4279, 1996.

P. Parnet et al., "IL–1Rrp is a novel receptor–like molecule similar to the type I interleukin–1 receptor and AJ its homologues T1/ST2 and IL–1R AcP", The Journal of Biological Chemistry, vol. 271, No. 8, pp 3967–3970, Feb. 23, 1996.

S. Mizushima et al., "pEF–BOS a powerful mammalian expression vector", Nucleic Acids Research, vol. 18, No. 17, 1990.

J. Minowada, " Leukemia cell lines", Caner Review, vol. 10, pp 1–18, 1988.

*Primary Examiner*—Yvonne Eyler
*Assistant Examiner*—Nirmal S. Basi
(74) *Attorney, Agent, or Firm*—Browdy and Neimark, PLLC

(57) ABSTRACT

Disclosed are a polypeptide (including that in soluble form) as receptor for a novel cytokine, i.e., interleukin-18, a DNA encoding the polypeptide, and the uses of the polypeptide including pharmaceutical and neutralizer to interleukin-18. Pharmaceuticals with the polypeptide is useful to treat and prevent autoimmune and allergic disease because it suppresses and regulates excessive immunoreaction.

8 Claims, 7 Drawing Sheets

Lane 1 : Molecular weight markers
Lane 2 : Sample (with monoclonal antibody)
Lane 3 : Sample (without monoclonal antibody)
Lane 4 : Molecular weight markers

POLYPEPTIDES THAT BIND INTERLEUKIN-18 (IL-18)

This is a divisional of application Ser. No. 08/996,338, filed Dec. 22, 1997, now issued as U.S. Pat. No. 6,087,116, the entire content of which is hereby incorporated by reference.

BACKGROUND OF THE INVENTION

1. Field of the Invention

This invention relates to a novel receptor protein which recognizes a cytokine, more particularly, to a novel polypeptide which recognizes interleukin-18 (hereinafter abbreviated as "IL-18").

2. Description of the Prior Art

IL-18 is a type of cytokine or substance which mediates signal transduction in immune system. As seen in Japanese Patent Kokai Nos. 27,189/96 and 193,098/96 and Haruki Okamura et al., *Nature*, Vol.378, No.6, 552, pp.88–91 (1995), IL-18 was provisionally designated as "interferon-gamma inducing factor" immediately after its discovery: This designation was changed later into "IL-18" in accordance with the proposal in Shimpei Ushio et al., *The Journal of Immunology*, Vol.156, pp.4,274–4,279 (1996). IL-18 in mature form consists of 157 amino acids and possesses properties of inducing in immunocompetent cells the production of interferon-gamma (hereinafter abbreviated as "IFN-γ") which is known as useful biologically-active protein, as well as of inducing and enhancing the generation and cytotoxicity of killer cells. Energetic studies are now in progress to develop and realize various uses of IL-18 in pharmaceuticals such as antiviral, antimicrobial, antitumor and anti-immunopathic agents which have been in great expectation because of these properties of IL-18.

As described above, in nature, cytokines including IL-18 are produced and secreted as substances responsible for signal transduction in immune system. Therefore, excessive amounts of cytokines may disturb the equilibria in immune system when they are produced or administered in the body of mammals. The surface of usual mammalian cells may bear certain sites or "receptors" which are responsible for recognition of cytokines: Secreted cytokines transduce no signal in cells till they are bound to the receptors. In normal immune system, there would be definite equilibria between respective cytokines and their receptors. Thus, in this field, with the purpose of developing and realizing IL-18 as pharmaceuticals, in addition to the clarification of physiological activities of IL-18, an expedited establishment of mass production and characterization of IL-18 receptor (hereinafter abbreviated as "IL-18R") have been in great expectation.

SUMMARY OF THE INVENTION

In view of the foregoing, the first object of this invention is to provide a polypeptide as IL-18R which can be easily prepared on a large scale.

The second object of this invention is to provide uses of such polypeptide as pharmaceuticals.

The third object of this invention is to provide a DNA which encodes the polypeptide.

The fourth object of this invention is to provide a process to prepare the polypeptide.

The fifth object of this invention is to provide an agent to neutralize IL-18 using the polypeptide.

The sixth object of this invention is to provide a method to neutralize IL-18 using the polypeptide.

We energetically and extensively screened various means which might attain these objects, eventually resulting in the finding that a substance which recognized IL-18 was present in L428 cell, a type of lymphoblastoid cell derived from a patient with Hodgkin's disease. We isolated and characterized this substance, revealing that its nature was proteinaceous, as well as that it well recognized and bound IL-18 even when in isolated form. It was also found that the IL-18R thus identified was efficacious in treatment and prevention of various diseases resulting from excessive immunoreaction, such as autoimmune diseases, because in mammals including human, IL-18R recognized and neutralized IL-18 which activated immune system. Further, we have energetically studied L428 cell using as probe some partial amino acid sequences of the IL-18R, resulting in obtainment of a DNA which did encode IL-18R. We confirmed that a polypeptide obtained by bringing such DNAs into expression in artificial manner well recognized IL-18 and shared some essential physiological activities with the IL-18R separated from L428 cell, as well as that it was preparable in desired amounts by recombinant DNA techniques using such DNA. Thus we accomplished this invention.

More particularly, this invention attains the first object with a polypeptide as IL-18R, which is obtainable through gene expression.

This invention attains the second object with an agent for IL-18R susceptive diseases, which contains as effective ingredient such polypeptide.

This invention attains the third object with a DNA which encodes the polypeptide.

This invention attains the forth object with a process to prepare polypeptide, comprising bringing into expression a DNA which encodes the polypeptide, and collecting the resultant polypeptide.

This invention attains the fifth object with an agent to neutralize IL-18, which contains as effective ingredient the polypeptide.

This invention attains the sixth object with a method to neutralize IL-18, characterized by allowing the polypeptide to act on IL-18.

L428 cell, which is feasible in this invention, have been deposited in the Patent Microorganism Depository, National Institute of Bioscience and Human-Technology, Agency of Industrial Science and Technology, 1–3, Higashi 1 chome, Tsukuba-shi, Ibaraki-ken, 305, Japan, under the accession number of "FERM BP-5777" on and after Dec. 24th, 1996.

Figure 1:
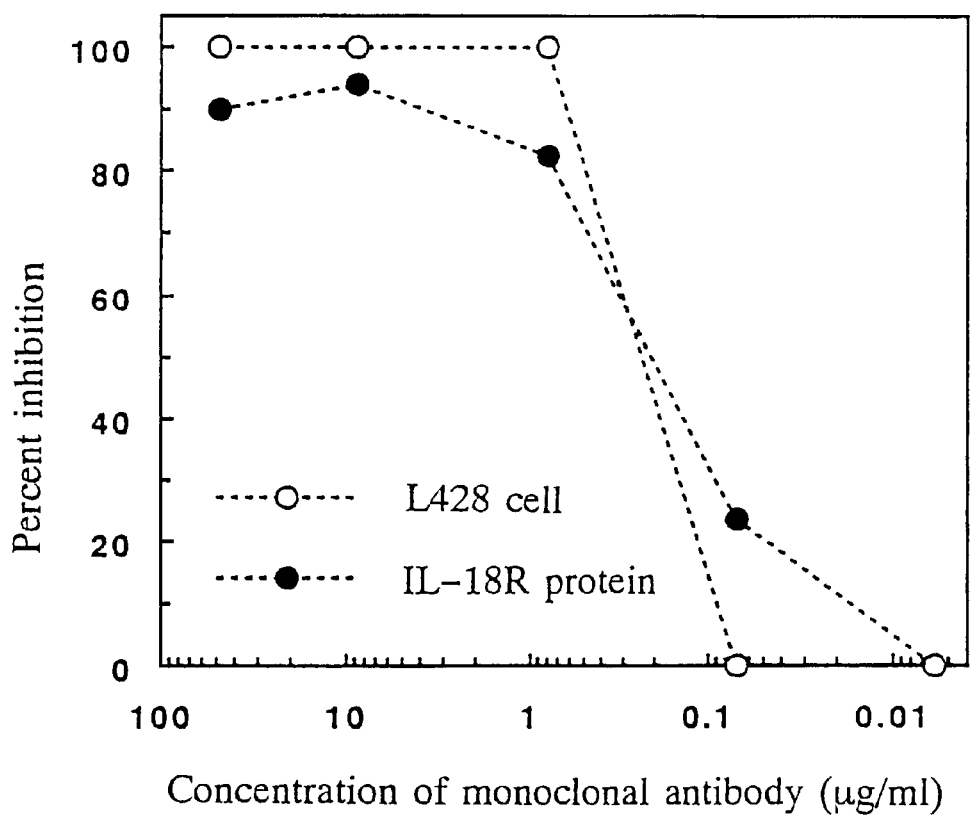
FIG. 1 shows that the monoclonal antibody MAb #117-10C binds to L428 cells and IL-18R while competing with IL-18.

Throughout the Figures, the symbol "Pcmv" indicates the cytomegalo virus promotor; "EF1αP", the elongation factor promotor; "IL-18R cDNA", the cDNA encoding the polypeptide of this invention; "EFHIL18R-14 cDNA", the cDNA encoding the soluble polypeptide according to this invention; "HIL18RD1-2-H cDNA", the cDNA encoding the soluble polypeptide of human origin according to this invention; "HIL18RD1-H cDNA", the cDNA encoding the soluble polypeptide of human origin according to this invention; and "EFMIL18RSHT cDNA", the cDNA encoding the soluble polypeptide of mouse origin according to this invention.

DETAILED DESCRIPTION OF THE INVENTION

This invention relates to a polypeptide as IL-18R, which is obtainable through gene expression. The polypeptide of human origin according to this invention usually contains as partial amino acid sequence(s) one or more amino acid sequences of SEQ ID NOs:12 to 19: As a whole, it contains a part or whole of the amino acid sequence of SEQ ID NO:20. While the polypeptide of mouse origin according to this invention usually contains a part or whole of the amino acid sequence of SEQ ID NO:21. Thus, the wording "polypeptide" as referred to in this invention shall include, in addition to those which wholly contain the amino acid sequence of either SEQ ID NO:20 or 21, for example, those which contain the same amino acid sequence but with addition of one or more amino acids, in particular, those which contain one or more amino acids linked to the C- and/or N-termini in SEQ ID NO:20 or 21; those which contain the same amino acid sequence as in SEQ ID NOs:20 and 21 but with deletion of one or more amino acids, in particular, soluble polypeptides which contain the amino acid sequences of SEQ ID NOs:22 to 25; and those which contain either of the amino acid sequences as described above but with a saccharide chain, as far as they are obtainable through gene expression and possess the essential functions of IL-18R. As to IL-18, those of human and mouse origins commonly consisting of 157 amino acids have been documented: Human IL-18 bears the amino acid sequence of SEQ ID NO:26 (where the amino acid with symbol "Xaa" represents either isoleucine or threonine), while mouse counterpart, the amino acid sequence of SEQ ID NO:27 (where the amino acid with symbol "Xaa" represents either methionine or threonine).

The polypeptide of this invention is usually prepared by applying recombinant DNA techniques, more particularly, by bringing into expression in artificial manner a DNA which encodes the polypeptide, and collecting the resultant polypeptide. This invention provides, in addition to a DNA which encodes the polypeptide, a process to prepare the polypeptide using recombinant DNA techniques: By practicing such a process according to this invention, desired amounts the polypeptide can be easily obtained.

The DNA which is used in this invention are those which originating natural sources, those which can be obtained by artificially modifying them and those which can be obtained through chemical synthesis, provided that they do encode the polypeptide. Generally, in this field, in case of artificially expressing DNAs which encode polypeptides, one may replace one or more nucleotides in the DNAs with different nucleotides and/or link an appropriate nucleotide sequence to the DNAs, with purpose of improving their expression efficiency and/or the physiological and physicochemical properties of the polypeptides. Such modifications are feasible in the DNA of this invention of course: For example, one can link to the 5'- and 3'-termini of the DNA as described above recognition sites for appropriate restriction enzymes, initiation and termination codons, promotors and/or enhancers, as far as the final polypeptide products do retain desired physiological activities. Thus, the wording "DNA" as referred to in this invention shall mean, in addition to those which encode any polypeptides as described above, those which are complementary thereto, and further those where one or more nucleotides have been replaced with different nucleotides while conserving the amino acid sequence.

To obtain such a DNA from natural sources, for example, mammalian cells including epithelial cells, endothelial cells, interstitial cells, chondrocytes, monocytes, granulocytes, lymphocytes, neurocytes and their established cell lines of human and mouse origins are screened with oligonucleotides as probe which can be prepared with reference to the amino acid sequences of SEQ ID NOs:12 to 25. Examples of preferred cells are cell lines which are obtained by establishing hemopoietic cells including lymphocytes, in particular, JM cells, HDLM-2 cells, MOLT-16 cells and PEER cells described in Jun Minowada, *Cancer Review*, Vol.10, pp.1–18 (1988), and lymphoblastoid cells such as L428 cell (FERM BP-5777), KG-1 cell (ATCC CCL-246) and U-937 cells (ATCC CRL-1593.2). The human and mouse DNAs obtained in this way usually contain a part or whole of respective nucleotide sequences of SEQ ID NOs:1 and 2. For example, as shown in SEQ ID NO:7, the DNA obtained from L428 cell, a type of lymphoblastoid cell derived from a patient with Hodgkin's disease, consists of the nucleotide sequence of SEQ ID NO:1 encoding the amino acid sequence of SEQ ID NO:20, and another nucleotide sequence encoding signal peptide which is linked to the 5'-terminal in the nucleotide sequence of the SEQ ID NO:1. Soluble polypeptides with the amino acid sequences of SEQ ID NOs:22 to 25 are usually encoded by respective nucleotide sequences of SEQ ID NOs:3 to 6, which are usually used in a form where, as shown in the nucleotide sequences of SEQ ID NOs:8 to 11, a nucleotide sequence encoding signal peptide is linked to the 5'-terminal in the nucleotide sequences of SEQ ID NOs:3 to 6. Such a DNA can be also obtained through usual chemical synthesis, and in any case, DNAs can be amplified to desired levels by PCR method once they become available. By the way, the amino acid sequences of SEQ ID NOs:20 and 21 are described along with the amino acid sequences for signal peptides in P. Parnet et al., *The Journal of Biological Chemistry*, Vol.271, pp.3,967–3,970 (1996): This paper however makes neither suggestion nor teaching that the polypeptides with the amino acid sequences of SEQ ID NOs:20 and 21 do function as IL-18R.

Such DNA expresses the polypeptide when introduced into an appropriate host of microbe, animal or plant origin. The DNA of this invention is usually prepared into a recombinant DNA prior to introduction into host. Such recombinant DNA, which consists of the DNA of this invention and an autonomously replicable vector, can be easily prepared with usual recombinant DNA techniques, provided that the DNA is available. Examples of vectors which can receive the DNA of this invention are plasmid vectors including pKK223-3, pcDNAI/Amp, BCMGSNeo, pcDL-SRα, pKY4, pCDM8, pCEV4, pME18S and pEF-BOS. Autonomously replicable vectors usually comprises other nucleotide sequences, for example, promotor, enhancer, replication origin, terminator of transcription, splicing sequence and/or selection marker which facilitate the expression of the DNA of this invention in particular hosts. Expression of the DNA becomes artificially regulatable upon external stimuli when it is used in combination with either heat shock protein promotor or interferon-a promotor as disclosed in Japanese Patent Kokai No. 163,368/95 by the same applicant.

Conventional methods are feasible in the insertion of the DNA of this invention into such vector. More particularly, a gene with the DNA of this invention and an autonomously replicable vector are first digested with restriction enzyme and/or ultrasonication, then the resultant DNA and vector fragments are ligated. Ligation of DNA and vector fragments become much easier when genes and vectors are digested with restriction enzymes specific to particular nucleotides, for example, AccI, BamHI, BstXI, EcoRI, HindIII, NotI, PstI, SacI, SalI, SmaI, SpeI, XbaI and XhoI. To ligate DNA and vector fragments, they are first annealed, if necessary, then exposed to DNA ligase in vivo or in vitro. The recombinant DNA thus obtained is unlimitedly replicable in hosts of microbe and animal origins.

Such recombinant DNA is introduced into an appropriate host, prior to use in preparation of the polypeptide. Although conventional hosts of microbe, animal and plant origins are feasible in this invention, it is preferable to choose a host of yeast or mammalian origin in case that the final use of the polypeptide is pharmaceuticals. Examples of host cells of mammalian origin are epithelial cell, interstitial cell and hemopoietic cell of human, monkey, mouse and hamster origins, in particular, 3T3 cell (ATCC CCL-92), C127I cell (ATCC CRL-1616), CHO-K1 cell (ATCC CCL-61), CV-1 cell (ATCC CCL-70), COS-1 cell (ATCC CRL-1650), HeLa cell (ATCC CCL-2), MOP-8 cell (ATCC CRL-1709) and their mutant strains. To introduce the DNA of this invention into such a host, one can employ conventional methods, for example, DEAE-dextran method, calcium phosphate transfection method, electroporation method, lipofection method, microinjection method and viral infection method using retrovirus, adenovirus, herpesvirus and vaccinia virus. To select among the resultant transformants a clone which is capable of producing the polypeptide, the transformants are cultivated on culture medium, followed by selecting one or more clones where production of the polypeptide is observed. Recombinant DNA techniques using host cells of mammalian origin are detailed, for example, *Jikken-Igaku-Bessatsu, Saibo-Kogaku Handbook* (The handbook for the cell engineering), edited by Toshio KUROKI, Masaru TANIGUCHI and Mitsuo OSHIMURA, published by Yodosha. Co., Ltd., Tokyo, Japan (1992), and *Jikken-Igaku-Bessatsu, Biomanual Series 3, Idenshi-Cloning-Jikken-Ho* (The experimental methods for the gene cloning), edited by Takashi YOKOTA and Kenichi ARAI, published by Yodosha Co., Ltd., Tokyo, Japan (1993).

The transformant thus obtained produces and secretes the polypeptide inside and/or outside the host cell when cultivated on culture medium. Such cultivation is feasible with conventional culture media directed to cultivation of transformants, which are usually composed by adding to a bufferized water as base inorganic ions such as sodium ion, potassium ion, calcium ion, phosphoric ion and chloric ion; minor elements, carbon sources, nitrogen sources, amino acids and vitamins which meet to the metabolism of particular hosts; and, if necessary, sera, hormones, cell growth factors and cell adhesion factors. Particular media are, for example, 199 medium, DMEM medium, Ham's F12 medium, IMDM medium, MCDB 104 medium, MCDB 153 medium, MEM medium, RD medium, RITC 80-7 medium, RPMI-1630 medium, RPMI-1640 medium and WAJC 404 medium. One can obtain a culture product containing the polypeptide by inoculating on such a culture medium a transformant in an amount of $1 \times 10^4$–$1 \times 10^7$ cells/ml, preferably, $1 \times 10^5$–$1 \times 10^6$ cells/ml, and subjecting the transformant to suspension or monolayer culture at around 37° C. for 1 day to 1 week, preferably, 2 to 4 days while replacing the culture medium with a fresh preparation, if necessary. The culture product thus obtained usually contains about 1 μg/l to 1 mg/l polypeptide, dependently of the type of transformant and cultivation conditions.

The culture product obtained in this way is first subjected to ultrasonication, cell-lytic enzyme and/or detergent to disrupt cells, if necessary, then polypeptides are separated from the cells or cell debris by filtration and centrifugation, followed by purification. In the purification, a culture product which has been separated from cell or cell debris is subjected to conventional methods common in purification of biologically-active proteins, for example, salting-out, dialysis, filtration, concentration, fractional precipitation, ion-exchange chromatography, gel filtration chromatography, adsorption chromatography, isoelectric focusing chromatography, hydrophobic chromatography, reversed phase chromatography, affinity chromatography, gel electrophoresis and isoelectric focusing gel electrophoresis which are used in combination, if necessary. The purified polypeptide is then concentrated and lyophilized into liquid or solid to meet to its final use. The IL-18 and monoclonal antibody, disclosed in Japanese Patent Kokai No. 193,098/96 and Japanese Patent Application No. 356,426/96 by the same applicant, are very useful in purification of the polypeptide: Immunoaffinity chromatographies using these do yield a high-purity preparation of the polypeptide with minimized costs and labors.

The polypeptide of this invention exhibits a remarkable efficacy in treatment and prevention of various diseases resulting from excessive immunoreaction because in mammals including human, the polypeptide recognizes and binds IL-18 which may activate immune system. Immune system, which is in nature to defend living bodies from harmful foreign substances, may cause unfavorable results in living bodies because of its nature. When mammals receive a graft of organ, for example, skin, kidney, liver, heart and bone marrow, the rejection reaction and immunoreaction against alloantigen may activate T-cells, resulting in the occurrence of inflammation and proliferation of lymphocytes. Similar phenomena are observed in case that host receives the invasion by heteroantigens, for example, allergens, which are not recognized as self. In autoimmune diseases, allergic reactions are induced by substances which must be recognized as self. The polypeptide of this invention exhibits a remarkable efficacy in treatment and prevention of various diseases resulting from such an immunoreaction because the polypeptide suppresses or regulates the immunoreaction when administered in mammals including human. Thus, the wording "susceptive diseases" as referred to in this invention shall mean all the diseases resulting from augmented immunoreaction which can be treated and/or prevented by the direct or indirect action of IL-18R: Particular susceptive diseases are, for example, rejection reactions associated with a graft of organ as described above, autoimmune and allergic diseases including pernicious anemia, atrophic gastritis, insulin-resistant diabetes, Wegener granulomatosis, discoid lupus erythematosus, ulcerative colitis, cold agglutinin-relating diseases, Goodpasture's syndrome, primary biliary cirrhosis, sympathetic ophtalmitis, hyperthyroidism, juvenile onset type diabetes, Sjögren syndrome, autoimmune hepatitis, autoimmune hemolytic anemia, myasthenia gravis, systemic scleroderma, systemic lupus erythematosus, polyleptic cold hemoglobinuria, polymyositis, periarteritis nodosa, multiple sclerosis, Addison's disease, purpura hemorrhagica, Basedow's disease, leukopenia, Behcet's disease, climacterium praecox, rheumatoid arthritis, rheumatopyra, chronic thyroiditis, Hodgkin's disease, HIV-infections, asthma, atopic dermatitis, allergic nasitis, pollinosis and apitoxin-allergy. In addition, the polypeptide of this invention is efficacious in treatment and prevention of septic shock which results from production or administration of excessive IFN-γ.

Thus, the agent for susceptive disease, which contains as effective ingredient the polypeptides of this invention, would find a variety of uses as anti-autoimmune-diseases, anti-allergies, anti-inflammatories, immunosuppressants, hematopoietics, leukopoietics, thrombopoietics, analgesics and antipyretics directed to treatment and/or prevention of susceptive diseases as illustrated in the above. The agent according to this invention is usually prepared into liquid, suspension, paste and solid forms which contain the polypeptide in an amount of 0.00001–100 w/w %, preferably, 0.0001–20 w/w %, dependently on the forms of agents as well as on the types and symptoms of susceptive disease.

The agent for susceptive diseases according to this invention includes those which are solely composed of the polypeptide, as well as including those in composition with, for example, one or more physiologically-acceptable carriers, excipients, diluents, adjuvants, stabilizers and, if necessary, other biologically-active substances: Examples of such stabilizer are proteins such as serum albumins and gelatin; saccharides such as glucose, sucrose, lactose, maltose, trehalose, sorbitol, maltitol, mannitol and lactitol; and buffers which are mainly composed of phosphate or succinate. Examples of the biologically-active substances usable in combination are FK506, glucocorticoid, cyclophosphamide, nitrogen mustard, triethylenethiophosphoramide, busulfan, pheniramine mustard, chlorambucil, azathioprine, 6-mercaptopurine, 6-thioguanine, 6-azaguanine, 8-azaguanine, 5-fluorouracil, cytarabine, methotrexate, aminopterin, mitomycin C, daunorubicin hydrochloride, actinomycin D, chromomycin $A_3$, bleomycin hydrochloride, doxorubicin hydrochloride, cyclosporin A, L-asparaginase, vincristine, vinblastine, hydroxyurea, procarbazine hydrochloride, adrenocortical hormone and auri colloid; receptor antagonists to cytokines other than IL-18, for example, antibodies respectively against interleukin-1 receptor protein, interleukin-2 receptor protein, interleukin-5 receptor protein, interleukin-6 receptor protein, interleukin-8 receptor protein and interleukin-12 receptor protein; and antagonists respectively against TNF-α receptor, TNF-β receptor, interleukin-1 receptor, interleukin-5 receptor and interleukin-8 receptor.

The agent for susceptive diseases according to this invention includes pharmaceuticals in minimal dose unit: The wording "pharmaceutical in minimal dose unit" represents those which are prepared into a physically united form suitable for prescription and also allowed to contain the polypeptide in an amount corresponding to its single dose or multiple (up to 4-fold) or divisor (up to 1/40) thereof: Examples of such form are injection, liquid, powder, granule, tablet, capsule, sublingual, ophthalmic solution, nasal drop and suppository. The agent for susceptive diseases according to this invention can be administrated through both oral and parenteral routes to exhibit in each case a remarkable efficacy in treatment and prevention of susceptive diseases. More particularly, the polypeptide is administered through oral route or parenteral route such as intradermal, subcutaneous, intramuscular or intravenous route at a dose of about 1 μg/time/adult to about 1 g/time/adult, preferably, about 10 μg/time/adult to about 100 mg/time/adult 1 to 4 times/day or 1 to 5 times/week over 1 day to 1 year.

The DNA which encodes the polypeptide of this invention is useful in "gene therapies". Particularly, in usual gene therapies, the DNA of this invention is first inserted in a vector derived from virus such as retrovirus, adenovirus or adeno-associated virus and, alternatively, embedded in either cationic- or membrane fusible-liposomes, then the inserted or embedded DNA is directly injected in a patient with an IL-18R susceptive disease and, alternatively, introduced into lymphocytes, which have been collected from the patient, and implanted in the patient. In adoptive immuno gene therapies, by introducing the DNA of this invention into effector cells similarly as in the usual gene therapies, the cytotoxicity of effector cells against tumors and virus-infected cells is enhanced and this would strengthen adoptive immunotherapy. In tumor vaccine gene therapy, tumor cells, which have been extracted from a patient, are introduced with the DNA of this invention similarly as in the usual gene therapies, allowed to proliferate in vitro to a prescribed level and then self-transplanted to the patient: The transplanted tumor cells act as vaccine in the body of the patient, exhibiting a strong and antigen-specific antitumor immunity. Thus, the DNA of this invention exhibits a remarkable efficacy in gene therapies for various diseases including, for example, malignant tumors, vial diseases, infections and autoimmune diseases, as well as in suppression of rejection reaction and excessive immunoreaction associated with grafts of organs and allergic diseases. General procedures for gene therapies are detailed in *Jikken-Igaku-Bessatsu, Biomanual UP Series, Idenshichiryo-no-Kisogijutsu* (Basic techniques for the gene therapy), edited by Takashi SHIMADA, Izumi SAITO, and Keiya OZAWA, published by Yodosha Co., Ltd., Tokyo, Japan (1996).

Further, the polypeptide of this invention is useful in affinity chromatography and labelled assay directed to purification and detection of IL-18 because the polypeptide bears properties of recognizing and binding IL-18. In addition, the polypeptide of this invention, in particular, that in soluble form is useful in screening in vivo or in vitro agonists and antagonists to IL-18. Furthermore, the agent to neutralize IL-18 containing as effective ingredient the polypeptide and the method to neutralize IL-18 where IL-18 is exposed to the polypeptide are useful in treatment of various diseases which result from production and administration of excessive IL-18.

The following Examples are to illustrate the way of practicing this invention. The techniques employed in Examples 1 to 9 are common in this field as detailed, for example, *Jikken-Igaku-Bessatsu, Saibo-Kogaku Handbook* (The handbook for the cell engineering), edited by Toshio KUROKI, Masaru TANIGUCHI and Mitsuo OSHIMURA, published by Yodosha. Co., Ltd., Tokyo, Japan (1992), and *Jikken-Igaku-Bessatsu, Biomanual Series 3, Idenshi-Cloning-Jikken-Ho* (The experimental methods for the gene cloning), edited by Takashi YOKOTA and Kenichi ARAI, published by Yodosha Co., Ltd., Tokyo, Japan (1993).

EXAMPLE 1

Preparation and Characterization of IL-18R

EXAMPLE 1-1

Preparation of IL-18R

Newborn hamsters were intraperitoneally injected with an anti-lymphocyte antibody of rabbit origin to suppress their possible immunoreaction, subcutaneously injected at their dorsal areas with about $5 \times 10^5$ cell/animal of L428 cells (FERM BP-5777), a type of lymphoblastoid cell derived from a patient with Hodgkin's disease, and fed in usual manner for 3 weeks. The tumor masses, subcutaneously occurred, about 10 g each, were extracted, disaggregated and washed in usual manner in serum-free RPMI-1640 medium (pH 7.4), thus obtaining proliferated cells.

The proliferated cells were added with a mixture solution (volume ratio of 9:1) of 0.83 w/v % $NH_4Cl$ and 170 mM Tris-HCl buffer (pH 7.7) in an amount 10-fold larger than the wet weight of the cells, stirred and collected by centrifugation at 2,000 rpm for 10 minutes. The cells were then suspended in an appropriate amount of phosphate buffered saline (hereinafter abbreviated as "PBS"), stirred, collected by centrifugation at 2,000 rpm, resuspended to give a cell density of about $1 \times 10^8$ cells/ml in 10 mM Tris-HCl buffer (pH 7.2) with 1 mM $MgCl_2$ and disrupted with "POLYTRON", a cell disrupter commercialized by Kinematica AG, Littau/Lucerne, Switzerland. The resultant was added with 10 mM Tris-HCl buffer (pH 7.2) containing both 1 mM $MgCl_2$ and 1 M sucrose to give a final sucrose concentration of 0.2 M, and centrifuged at 1,000 rpm to collect the supernatant which was then centrifuged at 25,000 rpm for 60 minutes, followed by collecting the precipitate. The precipitate was added with adequate amounts of 12 mM 3-[(3-cholamidopropyl)dimethylammonio]-1-propanesulfonic acid (hereinafter abbreviated as "CHAPS"), 10 mM ethylenediaminetetraacetatic acid (hereinafter abbreviated as "EDTA") and 1 mM phenylmethylsulfonylfluoride, stirred at 4° C. for 16 hours, and centrifuged at 25,000 rpm for 60 min, followed by collecting the supernatant.

The supernatant was charged to a column of "WHEAT GERM LECTIN SEPHAROSE 6B", a gel product for affinity chromatography commercialized by Pharmacia LKB Biotechnology AB, Uppsala, Sweden, pre-equilibrated in PBS with 12 mM CHAPS, and the column was washed with PBS containing 12 mM CHAPS, and then charged with PBS containing both 0.5 M N-acetyl-D-glucosamine and 12 mM CHAPS while monitoring the protein content in the eluate with the absorbance of ultraviolet at a wave length of 280 nm. The fractions with an absorbance of 0.16–0.20 were collected and pooled, thus obtaining about 25 liters of aqueous solution with a protein content of about 1 mg/ml per $10^{12}$ starting cells.

A small portion of the solution was sampled, added with 4 ng human IL-18 which had been $^{125}$I-labelled in usual manner, incubated at 4° C. for 1 hour, added with appropriate amounts of "POLYETHYLENE GLYCOL 6000", a polyethylene glycol preparation with an averaged molecular weight of 6,000 daltons, commercialized by E. Merck, Postfach, Germany, and allowed to stand under ice-chilling conditions for 30 minutes to effect binding reaction. The reaction product was centrifuged at 6,000 rpm for 5 minutes and the resultant precipitate was collected to determine the level of radioactivity. In parallel, there was provided another sections as control in which 3 μg non-labelled human IL-18 was used along with $^{125}$I-labelled human IL-18 and treated similarly as above. Comparison with control revealed that the radioactivity of the precipitate from the sample solution was significantly higher. This indicated that the aqueous solution obtained in the above did contain IL-18R and the I-18R recognized and bound IL-18 when exposed to IL-18.

EXAMPLE 1-2

Binding Ability to Monoclonal Antibody

L428 cells (FERM BP-5777) were suspended in RPMI-1640 medium (pH7.4), supplemented with 0.1 v/v % bovine serum albumin and also containing 0.1 v/v % $NaN_3$, to give a cell density of $4 \times 10^7$ cells/ml, while monoclonal antibody MAb #117-10C specific to human IL-18R, obtained by the method described in Japanese Patent Application No. 356, 426/96 by the same applicant, was dissolved in another preparation of RPMI-1640 medium supplemented with 0.1 w/v% bovine serum albumin to give different concentrations of 0.019 μg/ml, 0.209 μg/ml, 2.3 μg/ml, 25.3 μg/ml and 139.5 μg/ml.

Fifty microliter aliquots of the cell suspension prepared in the above were mixed with 50 μl of either solution with different monoclonal antibody concentrations, agitated at 4° C. for 2 hours, added with 50 μl of RPMI-1640 medium supplemented with 0.1 v/v % bovine serum albumin and also containing 4 ng $^{125}$I-labelled human IL-18 prepared in usual manner, and agitated at the same temperature for an additional 30 minutes. Subsequently, each cell suspension was added with 200 μl mixture solution (volume ratio 1:1) of dibutylphthalate and diocthylphtalate and centrifuged at 10,000 rpm and 20° C. for 5 minutes, followed by collecting the resultant precipitates containing the cells which were then determined for radioactivity using "MODEL ARC-300", a gamma-ray counter commercialized by Aloka Co., Ltd, Tokyo, Japan.

In parallel, there were provided additional two sections where the monoclonal antibody was neglected, while 4 ng $^{125}$I-labelled human IL-18 was treated similarly as in the sample testing section with or without 4 micrograms of non-labelled human IL-18 (hereinafter referred to as "non-specific binding section" and "whole binding section" respectively). The levels of radioactivity found in "non-specific binding section" and "whole binding section" were put in Formula 1 together with that found in the sample testing section to calculate percent inhibition. The results were as shown in FIG. 1.

$$\text{Percent Inhibition} = \frac{(\text{Whole binding}) - (\text{Testing})}{(\text{Whole binding}) - (\text{Non-specific binding})} \times 100 \quad \text{Formula 1}$$

Fifty microliter aliquots of an IL-18R in aqueous solution obtained by the method in Example 1-1 were added with 50 μl solution with different concentrations for monoclonal antibody MAb #117-10C prepared similarly as above, agitated at 4° C. for 2 hours, added with 4 ng $^{125}$I-labelled human IL-18, and agitated at 4° C. for an additional 30 minutes. Subsequently, each mixture was added with 50 μl of 4 mg/ml γ-globulin, allowed to stand under ice-chilling conditions for 30 minutes, added with 250 μl of PBS with 20 w/v % polyethylene glycol, allowed to stand under ice-chilling conditions for an additional 30 A minutes, and centrifuged at 6,000 rpm at 4° C. for 5 minutes, followed by collecting the resultant precipitates which were then determined for radioactivity similarly as above.

At the same time, there were provided additional two sections where the monoclonal antibody was neglected, while 4 ng of $^{125}$I-labelled human IL-18 were treated similarly as in the sample testing section with or without 4 μg of non-labelled human IL-18 (hereinafter referred to as "whole binding section" and "non-specific binding section" respectively). The levels of radioactivity found in these two section were put in Formula 1 together in that found in the sample testing section to calculate percent inhibition. The results were as shown in FIG. 1.

As seen in FIG. 1, in both cases of using L428 cell and IL-18R in solution, the binding of IL-18 to L428 cell and IL-18R were inhibited much more as the concentration of monoclonal antibody MAb #117-10C elevated. This indicated that the monoclonal antibody MAb #117-10C was bound to the possible IL-18R on the surface of L428 cell in a fashion competing with IL-18, as well as that the aqueous solution obtained by the method in Example 1-1 did contain a protein capable of recognizing IL-18 or IL-18R and the monoclonal antibody MAb #117-10C specifically reacted with the IL-18R.

EXAMPLE 1-3

Western Blotting

A portion of the IL-18R in aqueous solution obtained by the method in Example 1-1 was sampled, added with ⅔ volume of a mixture solution of 2.5 w/v % sodium dodecyl sulfate and 50 v/v % glycerol, incubated at 37° C. for 1 hour, and separated into respective proteinaceous components on conventional SDS-PAGE using 10–20% gradient gel but using no reducing agent. The proteinaceous components on the gel were transferred in usual manner to a nitrocellulose membrane which was then soaked for 1 hour in an appropriate amount of 50 mM Tris-HCl buffer (pH7.5) with 10 μg/ml of monoclonal antibody MAb #117-10C obtained by the methods described in Japanese Patent Application No. 356,426/96 by the same applicant, 10 v/v % "BLOCK ACE", an immobilizing agent commercialized by Dainippon Seiyaku Co., Ltd., Osaka, Japan, and 0.05 v/v % "TWEEN 20", a detergent commercialized by City Chemical Corp., New York, U.S.A., and washed in 50 mM Tris-HCl buffer (pH7.5) with 0.05 v/v % Tween 20 to remove the remaining antibody. The membrane was then soaked in Tris-HCl buffer (pH 7.5) with an appropriate amount of an anti-mouse immunoglobulin antibody of rabbit origin prelabelled with horse radish peroxidase, 10 v/v % "BLOCK ACE" and 0.05 v/v % "TWEEN 20" for 1 hour to effect reaction, washed in 50 mM Tris-HCl buffer (pH 7.5) with 0.05 v/v % "TWEEN 20" and developed using "ECL kit", a kit for development commercialized by Amersham Corp., Arlington Heights, U.S.A.

At the same time, there was provided another section without the monoclonal antibody MAb #117-10C as control and it was treated similarly as above. The molecular weight markers were bovine serum albumin (67,000 daltons), ovalbumin (45,000 daltons), carbonic anhydrase (30,000 daltons), trypsin inhibitor (20,100 daltons) and α-lactoalbumin (14,000 daltons). The results were as shown in FIG. 2.

Figure 2:
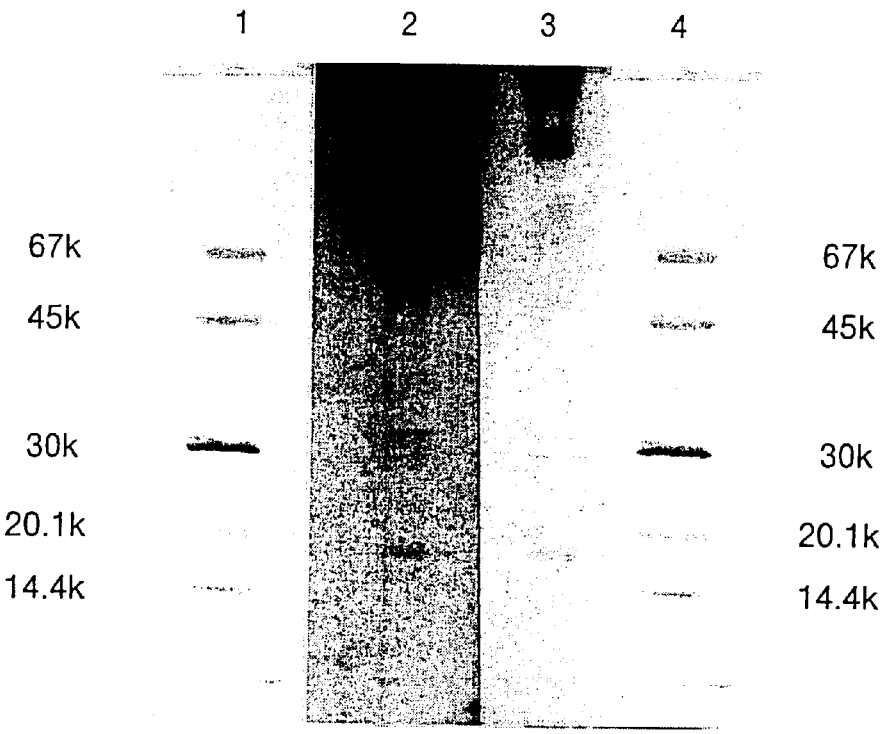
FIG. 2 is an image of intermediate tone given on display, which shows IL-18R on gel electrophoresis visualized by the Western blotting method using the monoclonal antibody MAb #117-10C.

In the gel electrophoresis in FIG. 2, Lane 2 (with monoclonal antibody) bore a distinct band of IL-18R which was never found in Lane 3 (without monoclonal antibody).

EXAMPLE 1-4

Inhibition of IL-18 Activity

KG-1 cells (ATCC CCL246), an established cell line derived from a patient with acute myelogenous leukemia, were suspended in RPMI-1640 medium (pH 7.2), supplemented with 10 v/v % fetal bovine serum and also containing 100 μg/ml kanamycin and 18.8 mM Na$_2$HPO$_4$, to give a cell density of 1×10$^7$ cells/ml, added with monoclonal antibody MAb #117-10C, obtained by the method described in Japanese Patent Application No. 356,426/96 by the same applicant, to give a concentration of 10 μg/ml and incubated at 37° C. for 30 minutes.

Figure 3:
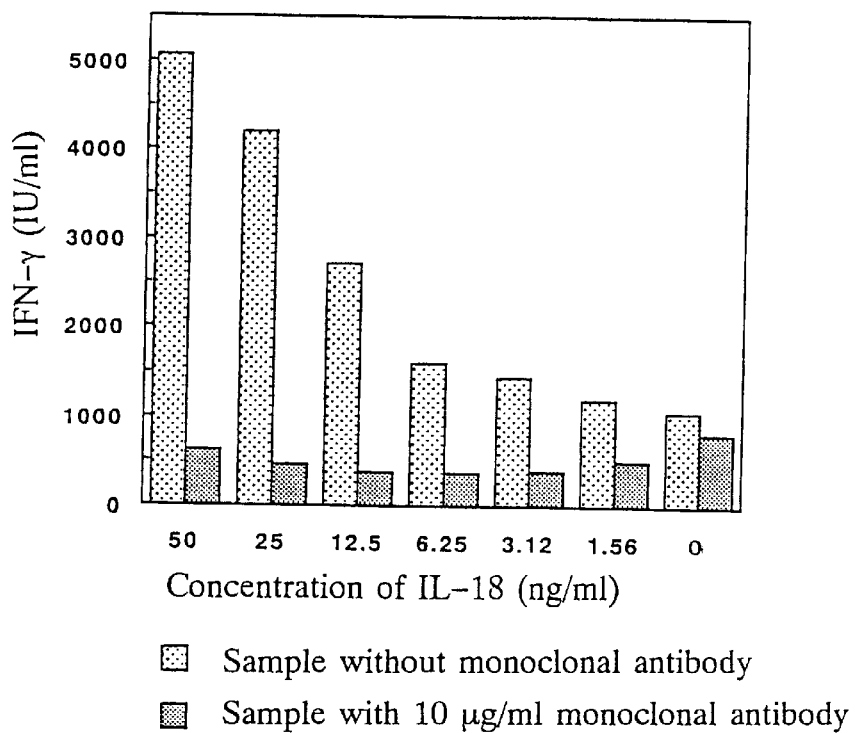
FIG. 3 shows the inhibitory action of the monoclonal antibody MAb #117-10C on the activity of IL-18.

The KG-1 cells in suspension were distributed on 96-well microplate to give respective amounts of 50 μl/well, added with 50 μl of human IL-18 which had been dissolved in a fresh preparation of the same medium to give respective concentrations of 0 ng/ml, 1.56 ng/ml, 3.12 ng/ml, 6.25 ng/ml, 12.5 ng/ml and 25 ng/ml, further added with 50 μl/well of 5 μg/ml lipopolysaccharide in a fresh preparation of the above medium, and incubated at 37° C. for 24 hours, after which each supernatant was collected and determined for IFN-γ content by conventional enzyme immunoassay. In parallel, there were provided additional sections without the monoclonal antibody MAb #117-10C for respective IL-18 concentrations as control and they were treated similarly as above. The results were as shown in FIG. 3. The IFN-γ contents in FIG. 3 were calibrated with reference to the standardized IFN-γ preparation Gg23-901-530 available from the International Institute of Health, USA, and expressed in the International Unit(IU).

The results in FIG. 3 indicated that the presence of monoclonal antibody MAb #117-10C inhibited the induction of IFN-γ by IL-18 in KG-1 cell as immunocompetent cell. This also indicated that monoclonal antibody MAb #117-10C blocked the IL-18R on the surface of KG-1 cell in a fashion competing with Il-18, thus preventing the signal transduction of IL-18 to KG-1 cell.

EXAMPLE 1-5

Purification of IL-18R

Seventy-eight milligrams of a monoclonal antibody MAb #117-10C, obtained by the method described in Japanese Patent Application No. 356,426/96 by the same applicant, was dissolved in an appropriate amount of distilled water and the solution was dialyzed against borate buffer (pH 8.5) with 0.5 M NaCl at 4° C. for 16 hours. Thereafter, in usual manner, an appropriate amount of "CNBr-ACTIVATED SEPHAROSE 4B", a CNBr-activated gel, commercialized by Pharmacia LKB Biotechnology AB, Uppsala, Sweden, was added to the dialyzed solution and allowed to react at 4° C. for 18 hours under gentle stirring conditions to immobilize the monoclonal antibody MAb #117-10C on the gel.

The gel was packed into column in a plastic cylinder, equilibrated with 2 mM CHAPS, charged with an IL-18R in aqueous solution obtained by the method in Example 1-1, and applied with PBS with 12 mM CHAPS to remove non-adsorbed components. The column was then applied with 35 mM ethylamine containing 2 mM CHAPS (pH 10.8) while collecting the eluate in every 8 ml fractions which were then checked for presence of IL-18R by the method in Example 1-1 using $^{125}$I-labelled human IL-18. The chromatogram obtained in this operation was as shown in FIG. 4.

Figure 4:
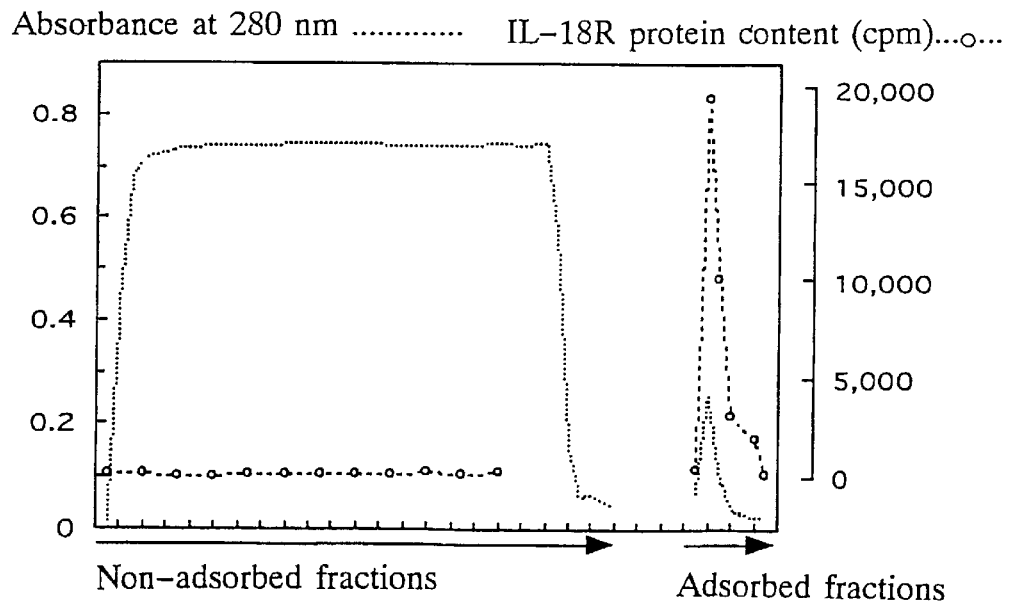
FIG. 4 is the chromatogram obtained by applying to IL-18R an immunoaffinity chromatography using the monoclonal antibody MAb #117-10C.

As seen in FIG. 4, IL-18R was eluted in a single sharp peak when immunoaffinity chromatography using monoclonal antibody MAb #117-10C was applied to a mixture of IL-18R and contaminants such as the aqueous solution of IL-18R in Example 1-1. The fractions corresponding to this single peak were collected, pooled and lyophilized, thus obtaining a purified IL-18R in solid form.

Thereafter, a portion of the purified IL-18R was sampled, incubated in PBS at 100° C. for 5 minutes, and determined for residual activity by the method in Example 1-2, resulting in no binding to IL-18 which proved that IL-18R was inactivated by heating. This would support that the nature of this receptor is proteinaceous.

Further, a portion of the purified IL-18R obtained in the above was dissolved in an appropriate amount of PBS, dialyzed against PBS at ambient temperature overnight, added with an appropriate amount of $^{125}$I-labelled human IL-18 prepared by the method in Example 1-1 and 1 mM "BS³", a polymerizing agent commercialized by Pierce, Rockford, U.S.A., and allowed to stand at 0° C. for 2 hours to form a conjugate of IL-18R and $^{125}$I-labelled human IL-18. The reaction mixture was added with Tris-HCl buffer (pH7.5), allowed to stand at 0° C. for an additional 1 hour to suspend the conjugation reaction, separated into respective proteinaceous components on SDS-PAGE using a set of molecular weight markers and dithiothreitol as reducing agent, and subjected to autoradiogram analysis.

The apparent molecular weight for this conjugate of IL-18R and $^{125}$I-labelled human IL-18 was about 50,000 to 200,000 daltons when estimated with reference to the mobility of molecular weight markers on the autoradiogram. Since the molecular weight of IL-18 is about 20,000 daltons, the molecular weight of IL-18R can be estimated about 30,000–180,000 daltons on the assumption that IL-18R binds one human IL-18 molecule.

EXAMPLE 1-6

Peptide Mapping of IL-18R

A purified IL-18R obtained by the method in Example 1-5 was electrophoresed on SDS-PAGE using 7.5 w/v % gel with 2 w/v % dithiothreitol as reducing agent, and the gel was then soaked for 5 minutes in a mixture solution of 40 v/v % aqueous methanol and 1 v/v % acetic acid with 0.1 w/v % Coomassie Brilliant Blue for development, and soaked for an additional 2 hours for destaining in the same solution but without Coomassie Brilliant Blue, after which the stained part in the gel, molecular weight of 80,000–110,000 daltons, was cut off, added with 50 v/v % aqueous acetonitrile containing 0.2 M $(NH_4)_2CO_3$ and repeatedly agitated at ambient temperature. Thereafter, the gel slices were lyophilized, added with 0.2 M $(NH_4)_2CO_3$ (pH 8.0), allowed to stand for 5 minutes to effect swelling, added with appropriate amounts of 1 mM hydrochloric acid with 0.1 µg/µl "SEQUENCING GRADE MODIFIED TRYPSIN", a reagent of trypsin commercialized by Promega Corp., Madison, U.S.A., and 0.2 M $(NH_4)_2CO_3$ (pH 8.9), and allowed to react at 37° C. overnight. After suspending with 10 v/v % aqueous acetic acid solution, the reaction mixture was added with a mixture solution of 0.1 v/v % trifluoroacetic acid and 60 v/v % aqueous acetonitrile and agitated at ambient temperature, after which the resultant supernatant was collected, concentrated in vacuo and centrifugally filtered, thus obtaining a concentrate with peptide fragments.

Figure 5:
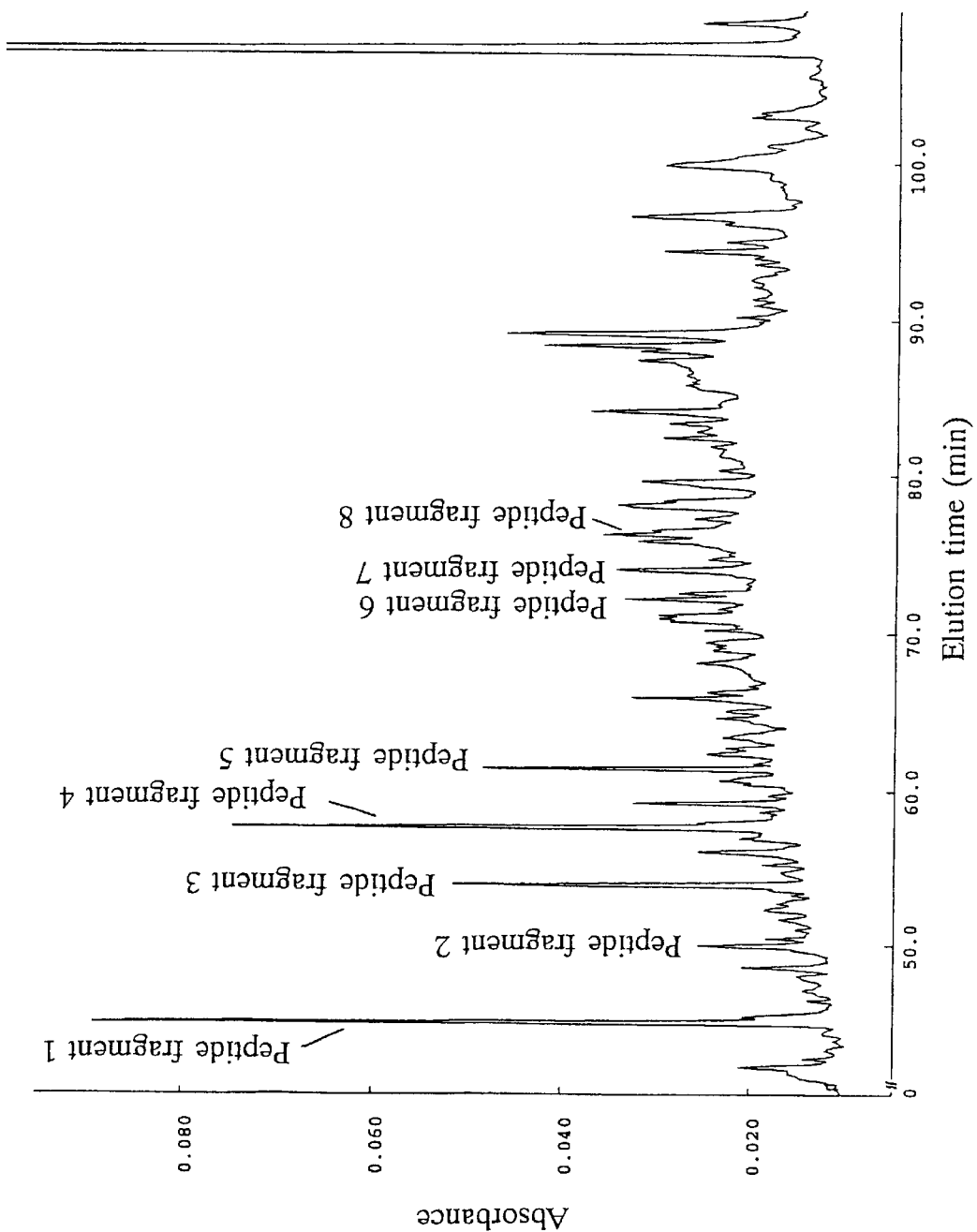
FIG. 5 is the peptide map of IL-18R.

The concentrate was charged to "µRPC C2/C18 SC2.1/10", a column for high-performance liquid chromatography commercialized by Pharmacia LKB Biotechnology AB, Uppsala, Sweden, pre-equilibrated with 0.065 v/v % trifluoroacetic acid, and then applied at a flow rate of 100 µl/min with 0.055 v/v % trifluoroacetic acid containing 80 v/v % aqueous acetonitrile under liner gradient of acetonitrile increasing from 0 to 80 v/v % over 160 minutes immediately after application of the eluent. While monitoring the absorbance at a wavelength of 240 nm, the eluate was fractioned to separately collect respective peptide fragments which eluted about 45, 50, 55, 58, 62, 72, 75 and 77 minutes after application of the eluent. The peptide fragments (hereinafter referred to as "peptide fragment 1", "peptide fragment 2", "peptide fragment 3", "peptide fragment 4", "peptide fragment 5", "peptide fragment 6", "peptide fragment 7" and "peptide fragment 8" in the order of elution) were analyzed in usual manner for amino acid sequence using "MODEL 473A", a protein sequencer commercialized by Perkin-Elmer Corp., Norwalk, U.S.A, revealing that the peptide fragments 1 to 8 bore the amino acid sequences of SEQ ID NOs:12 to 19 respectively. The peptide map obtained by this operation was as shown in FIG. 5.

EXAMPLE 2

Preparation of DNA

EXAMPLE 2-1

Preparation of Total RNA

In usual manner, L428 cells (FERM BP-5777) were suspended in RPMI-1640 medium (pH7.2) supplemented with 10 v/v % fetal bovine serum, and proliferated at 37° C. while scaling up the cultivation. When the cell density reached a prescribed level, the proliferated cells were collected, suspended in 10 mM sodium citrate (pH7.0) containing both 6M guanidine isothiocyanate and 0.5 w/v % sodium N-laurylsarcosinate, and then disrupted with a homogenizer.

Aliquots of 0.1 M EDTA (pH 7.5) containing 5.7 M $CsCl_2$ were placed in 35 ml-reaction tubes, poured with the cell disruptant obtained in the above in layer over the EDTA in each tube, and subjected to ultracentrifugation at 20° C. at 25,000 rpm for 20 hours to collect the RNA fraction. The RNA fraction was distributed in 15 ml-centrifugation tubes, added with an equivolume each of a mixture solution of chloroform/1-butanol (volume ratio 4:1), agitated for 5 minutes and centrifuged at 4° C. at 10,000 rpm for 10 minutes, after which the aqueous layer was collected, added with 2.5-fold volume of ethanol and allowed to stand at −20° C. for 2 hours to precipitate the total RNA. The precipitate was collected, washed with 75 v/v % aqueous ethanol, and then dissolved in 0.5 ml of sterilized distilled water to obtain a solution of the total RNA originating from L428 cell.

EXAMPLE 2-2

Preparation of mRNA

An aqueous solution containing total RNA solution obtained by the method in Example 2-1 was added with 0.5 ml of 10 mM Tris-HCl buffer (pH 7.5), containing both 1 mM EDTA and 0.1 w/v % sodium N-laurylsarcosinate, to bring the total volume to 1 ml. The mixture solution was added with 1 ml of "OLIGOTEX™-dT30 <SUPER>", a latex with an oligonucleotide of $(dT)_{30}$ commercialized by Japan Roche K. K., Tokyo, Japan, reacted at 65° C. for 5 minutes and rapidly cooled in an ice-chlling bath. Thereafter, the reaction mixture was added with 0.2 ml of 5 mM NaCl, incubated at 37° C. for 10 minutes, centrifuged at 10,000 rpm for 10 minutes to collect the resultant precipitate in pellet form which was then suspended in 0.5 ml of sterilized distilled water and incubated at 65° C. for 5 minutes to desorb the mRNA from the latex. The obtained solution was added with an appropriate amount of ethanol, and the resultant precipitate was collected and lyophilized to obtain a solid of mRNA.

EXAMPLE 2-3

Preparation of DNA Fragment Encoding Polypeptide

Four microliters of 25 mM $MgCl_2$, 2 µl of 100 mM Tris-HCl buffer (pH 8.3) containing 500 mM KCl, 1 µl of 25 mM dNTP mix, 0.5 µl of 40 units/µl ribonuclease inhibitor and 1 µl of 200 units/µl reverse transcriptase were placed in a 0.5 ml-reaction tube, added with 10 ng of an mRNA, obtained by the method in Example 2-2, along with an appropriate amount of random hexanucleotides, and added with sterilized distilled water to bring the total volume of 20 µl. The obtained mixture was incubated first at 42° C. for 20 minutes, then at 99° C. for 5 minutes to suspend the reaction, thus obtaining a reaction mixture containing a first strand cDNA.

Twenty microliters of the reaction mixture was added with 1 µl of 2.5 units/µl "CLONED Pfu POLYMERASE", a DNA polymerase commercialized by Stratagene Cloning Systems, California, U.S.A., 10 µl of the reaction buffer and 1 µl of 25 mM dNTP mix, both commercialized by Stratagene Cloning Systems, added with 0.1 µg each of oligonucleotides as sense and antisense primers having respective nucleotide sequences as shown with 5'-TCAGTCGACGCCACCATGAATTGTAGAGAA-3' (SEQ ID NO:28) and 5'-GAAGCGGCCGCATCATTAAGACTCGGAAAGAAC-3' (SEQ ID NO:29) which had been prepared on the basis of the amino acid sequence described in P. Parnet et al., *The Journal of Biological Chemistry*, Vol.271, pp.3967–3970 (1996), added with sterile distilled water to bring the total volume to 100 µl. The resultant mixture was subjected first to 3-time cycles of incubating at 95° C. for 1 minute, 42° C. for 2 minutes and 72° C. for 3 minutes in the given order, then to 35-time cycles of incubating at 95° C. for 1 minute, 60° C. for 2 minutes and 72° C. for 3 minutes in the given order to effect PCR reaction.

Fifty nanograms of the obtained PCR product was added with 1 ng of "pCR-Script Cam SK(+)", a plasmid vector commercialized by Stratagene Cloning Systems, California, U.S.A., and then subjected to ligation reaction at 16° C. for 2 hours using "DNA LIGATION KIT VERSION 2", a DNA ligation kit commercialized by Takara Syuzo, Co., Ltd., Otsu, Shiga, Japan, to insert the DNA fragment of the PCR product in the plasmid vector. A portion of the reaction product was sampled and used in usual manner to transform "XL1-BLUE MRFKAN", an *Escherichia coli* strain commercialized by Stratagene Cloning Systems, California, U.S.A.

EXAMPLE 3

Preparation of Recombinant DNA

Figure 6:
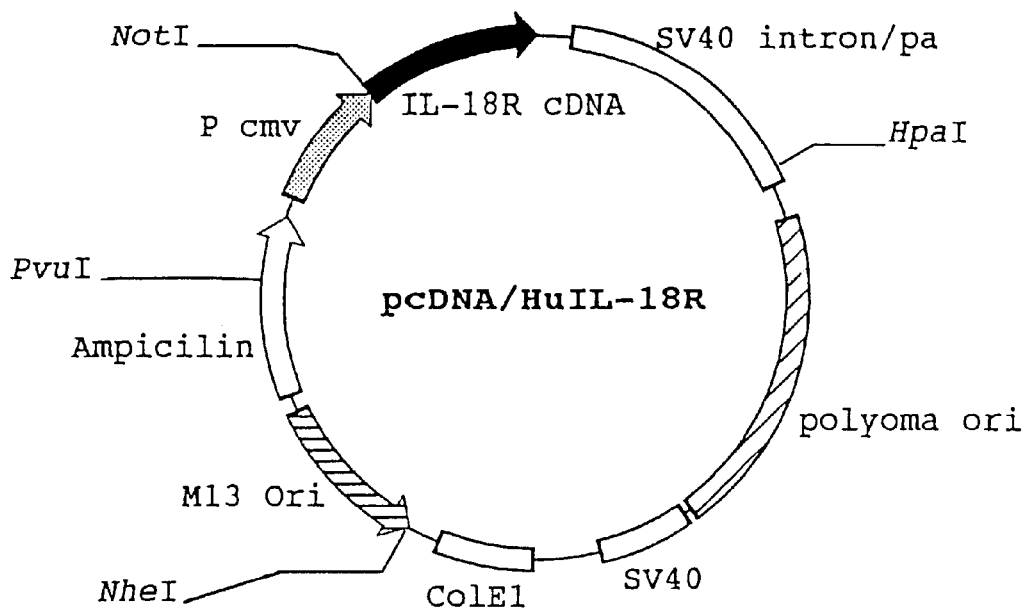
FIG. 6 shows the structure of the recombinant DNA "pcDNA/HuIL-18R" of this invention.

A transformant obtained by the method in Example 2-3 was inoculated in LB medium containing 30 µg/ml chloramphenicol and cultivated at 37° C. for 18 hours, after which the cells were collected from the culture and treated in usual manner to obtain the plasmid DNA. After confirming by the dideoxy method that the plasmid DNA contained the nucleotide sequence of SEQ ID NO:7, the plasmid DNA was exposed to both restriction enzymes NotI and SalI, and 100 ng of the obtained DNA fragment was added with 10 ng of "pcDNAI/Amp", a plasmid vector with a modified multiple cloning site, commercialized by Invitrogen Corporation, San Diego, U.S.A., which had been predigested with both restriction enzymes NotI and XhoI, and subjected to ligation reaction at 16° C. for 2 hours using "LIGATION KIT VERSION 2", a ligation kit commercialized by Takara Syuzo Co., Ltd., Otsu, Shiga, Japan. A portion of the reaction product was sampled and introduced in usual manner into "XL1-BLUE MRFKAN", a strain of *Escherichia coli* commercialized by Stratagene Cloning Systems, California, U.S.A., to obtain a transformant "cDNA/HuIL-18R" which contained a recombinant DNA "pcDNA/HuIL-18R" of this invention. The recombinant DNA "pcDNA/HuIL-18R" was analyzed in usual manner, revealing that in the recombinant DNA, a DNA "IL-18R cDNA", which contained the nucleotide sequence of SEQ ID NO:1 encoding the polypeptide of this invention, was linked downstream the cytomegalo virus promotor Pcmv, as shown in FIG. 6.

EXAMPLE 4

Preparation of Transformant

A transformant "cDNA/HuIL-18R" obtained by the method in Example 3 was inoculated in LB medium (pH 7.5) containing 100 µg/ml ampicillin and cultured at 37° C. for 18 hours, after which the cells were collected from the culture and treated in usual manner to obtain the plasmid DNA. Separately, COS-1 cell (ATCC CRL-1650), a fibroblastic cell line derived from a kidney of African green monkey was proliferated in usual manner, and 20 micrograms of the plasmid DNA obtained in the above was introduced by conventional electroporation method into $1\times10^7$ COS-1 cells to obtain transformant cells which contained the DNA of this invention.

EXAMPLE 5

Preparation of Polypeptide

DMEM medium (pH 7.2) supplemented with 10 v/v % fetal bovine serum was distributed in flat-bottomed culture bottles, inoculated with transformant cells, obtained by the method in Example 4, to give a cell density of $1\times10^5$ cells/ml, and cultured at 37° C. in 5 v/v % $CO_2$ incubator for 3 days. After removing the supernatant from the culture, PBS containing both 5 mM EDTA and 0.02 w/v % $NaN_3$ was placed in the culture bottles to desorb the proliferated cells.

After washing in PBS, the proliferated cells were rinsed in a buffer containing 20 mM HEPES, 10 mM KCl, 1.5 mM $MgCl_2$ and 0.1 mM EDTA (hereinafter referred to as "hypotonic buffer"), and suspended in a fresh preparation of the hypotonic buffer to give a cell density of $2\times10^7$ cells/ml. The cell suspension was homogenized with a Dounce-type homogenizer under ice-chilling conditions, and the resultant homogenate was centrifuged at 15,000 rpm at 5 minutes to remove both cell nuclei and intact cells, and dialyzed overnight against PBS containing 2 mM CHAPS.

The dialyzed product was charged to a column of immobilized monoclonal antibody MAb #117-10C, prepared by the method in Example 1-5, which was then applied with PBS containing 12 mM CHAPS to remove non-adsorbed components. Thereafter, the column was applied with 35 mM ethylamine (pH10.8) containing 2 mM CHAPS while collecting and fractionating the eluate. Each fraction was then checked for presence of the polypeptide of human origin by the method in Example 1-1 using $^{125}$I-labelled human IL-18, selected and pooled to obtain per $10^8$ starting cells about 2 ml of an aqueous solution which contained a polypeptide with the amino acid sequence of SEQ ID NO:20. The protein content in the solution was about 10 µg/ml.

The polypeptide thus obtained was studied for physicochemical properties by the methods in Example 1. As the result, the polypeptide obtained in this Example contained each amino acid sequence in SEQ ID NOs:12 to 19 as partial amino acid sequences, as well as exhibiting physiological activities which were similar to those of the IL-18R from L428 cell.

EXAMPLE 6

Soluble Polypeptide From Human Origin

EXAMPLE 6-1

Preparation of Recombinant DNA

One nanogram of a recombinant DNA "pcDNA/HuIL-18R" obtained by the method in Example 3, 10 μl of 10×PCR buffer and 1 μl of 25 mM dNTP mix were placed in 0.5 ml-reaction tube, added with 1 microliter of 2.5 units/microliter Pfu DNA polymerase, added with appropriate amounts of oligonucleotides as sense and antisense primers having respective nucleotide sequences as shown with 5'-TCAGTCGACGCCACCATGAATTGTAGAGAATTA-3' (SEQ ID NO:30) and 5'-GAAGCGGCCGCATCATTATCTTGTGAAGACGTG-3' (SEQ ID NO:31), and with sterile distilled water to bring the total volume to 100 μl. The resultant mixture was subjected first to 3-time cycles of incubating at 94° C. for 1 minute, 42° C. for 2 minutes and 72° C. for 3 minutes in the given order, then to 35-time cycles of incubating at 94° C. for, minute, 60° C. for 2 minutes and 72° C. for 3 minutes in the given order to effect PCR reaction.

Fifty nanograms of the obtained PCR product was added with 1 ng of "pCR-SCRIPT SK(+)", a plasmid vector commercialized by Takara Syuzo Co. Ltd., Otsu, Shiga, Japan, and reacted using "DNA LIGATION KIT VERSION 2", a DNA ligation kit commercialized by Takara Shuzo Co. Ltd., Otsu, Shiga, Japan, at 16° C. for 2 hours to insert the DNA fragment as the PCR product into the plasmid vector. A portion of the reaction product was sampled and "XL1-BLUE MRFKAN", a strain of *Escherichia Coli* commercialized by Stratagene Cloning Systems, California, U.S.A., was transformed therewith in usual manner.

Figure 7:
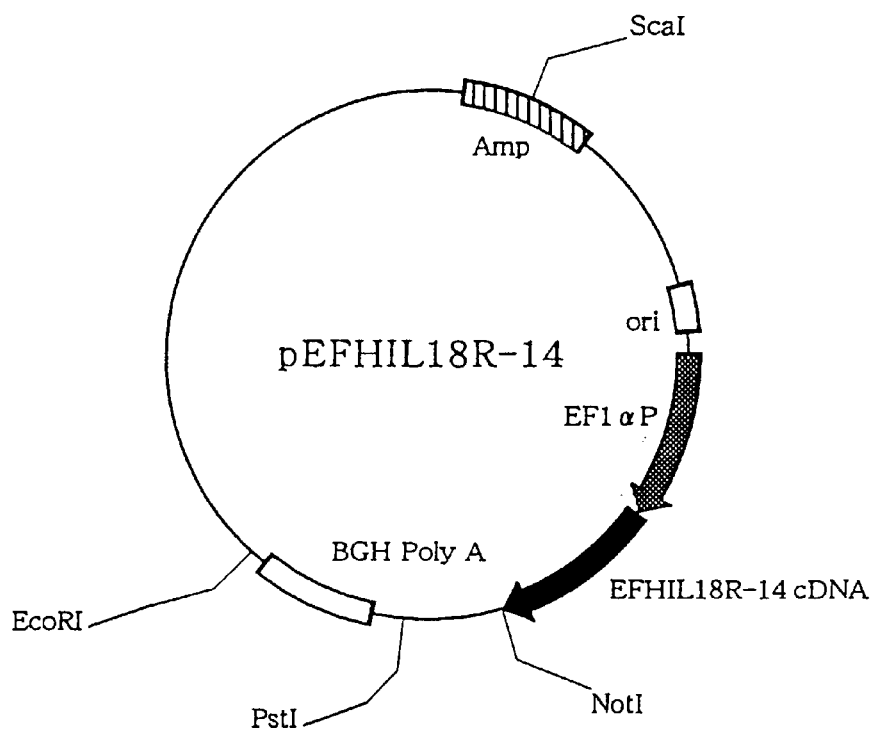
FIG. 7 shows the structure of the recombinant DNA "pEFHIL18R-14" of this invention.

The transformant obtained in the above was inoculated in LB medium (pH 7.5) containing 100 μg/ml ampicillin and cultivated at 37° C. for 18 hours, after which the cells were collected from the culture and treated in usual manner to obtain the plasmid DNA. After confirming by the dideoxy method that the plasmid DNA contained the nucleotide sequence of SEQ ID NO:10, the plasmid DNA was exposed to both restriction enzymes NotI and SalI, and 100 ng of the resultant DNA fragment was added with long of "pEF-BOS", a plasmid vector prepared in accordance with the method described in S. Mizushima, *Nucleic Acid Research*, Vol.18, No. 17, pp.5,332 (1990) with slight modification and also predigested with both restriction enzymes NotI and XhoI, and subjected to ligation reaction using "LIGATION KIT VERSION 2", a DNA ligation kit commercialized by Takara Shuzo Co., Ltd., Otsu, Shiga, Japan, at 16° C. for 2 hours. A portion of the reaction product was sampled and introduced in usual manner into "XL1-BLUE MRFKAN", a strain of *Escherichia coli* commercialized by Stratagene Cloning Systems, California, U.S.A., thus obtaining a transformant "EFHIL18R-14" which contained a recombinant DNA "pEFHIL18R-14" of this invention. The recombinant DNA "pEFHIL18R-14" was analyzed in usual manner, revealing that in the recombinant DNA, a cDNA "EFHIL18R-14 cDNA", which contained the nucleotide sequence of SEQ ID NO:6 encoding the polypeptide of this invention, was located downstream the elongation factor 1 promotor EF1αP as shown in FIG. 7.

EXAMPLE 6-2

Preparation of Transformant

A transformant "EFHIL18R-14" obtained by the method in Example 6-1 was inoculated in LB medium (pH 7.5) containing 100 μg/ml ampicillin and cultivated at 37° C. for 18 hours, after which the cells were collected from the culture and treated in usual manner to obtain the plasmid DNA. Separately, COS-1 cell (ATCC CRL-1650), a fibroblastoid cell line derived from a kidney of African green monkey, was proliferated in usual manner, and 20 micrograms of the plasmid DNA obtained in the above was introduced by conventional electroporation method into $1 \times 10^7$ COS-1 cells to obtain transformant cells which contained the DNA of this invention.

EXAMPLE 6-3

Preparation of Soluble Polypeptide

"ASF104", a serum-free nutrient culture medium commercialized by Ajinomoto Co., Inc., Tokyo, Japan, was distributed in flat-bottomed culture bottles, inoculated with ransformant cells, obtained by the method in Example 6-2, to givee a cell density of $1 \times 10^5$ cells/ml, and cultured in usual manner at 37° C. in 5 v/v % $CO_2$ incubator for 3 days. The supernatant was collected from the culture and charged to a column of an immobilized monoclonal antibody #117-10C prepared by the method in Example 1-5, after which the column was applied first with PBS containing 12 mM CHAPS to remove non-adsorbed components, then with 35 mM ethylamine (pH 10.8) containing 2 mM CHAPS while collecting and fractionating the eluate. Each fraction was checked for presence of human soluble polypeptide by the method in Example 1-1 using $^{125}$I-labelled human IL-18, selected and pooled to obtain per $10^8$ starting cells about 2 ml of an aqueous solution which contained a polypeptide with the amino acid sequence of SEQ ID NO:22. The protein content in the solution was about 10 μg/ml.

The soluble polypeptide thus obtained was studied for physicochemical properties by the method in Example 1. As the result, the soluble polypeptide obtained in this Example contained each amino acid sequences in SEQ ID NOs:12 to 17 and 19 as partial sequences, as well as exhibiting physiological activities which were similar to the IL-18R from L428 cell.

EXAMPLE 7

Soluble Polypeptide of Human Origin

Figure 8:
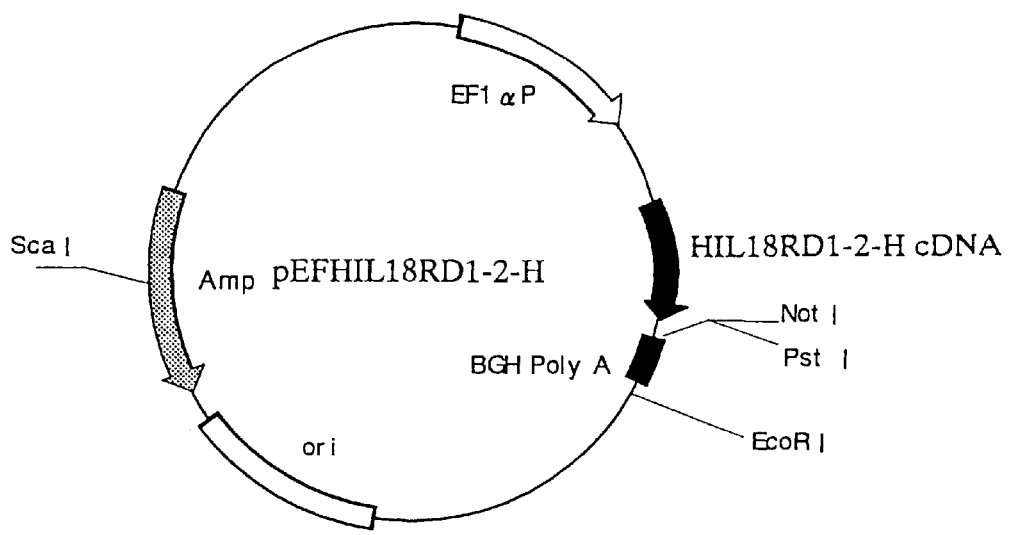
FIG. 8 shows the structure of the recombinant DNA "pEFHIL18RD1-2-H" of this invention.

One nanogram of an recombinant DNA "pEFHIL18R-14" obtained by the method in Example 6-1, 10 μl of 10×PCR buffer and 1 μl of 25 mM dNTP mix were placed in 0.5 ml-reaction tube, added with 1 μl of 2.5 units/μl Pfu DNA polymerase, further added with appropriate amounts of oligonucleotides as sense and antisense primers having respective nucleotide sequences as shown with 5'-TCAGTCGACGCCACCATGAATTGTAGAG-3' (SEQ ID NO:32) and 5'-GAAGCGGCCGCTCATTAGTGATGGTGATGGTG ATGTGCAACATGGTTAAGCTT-3' (SEQ ID NO:33), and filled up to 100 μl with sterile distilled water. The resultant mixture was subjected first to 3-time cycles of incubating at 94° C. for 1 minute, 42° C. for 2 minutes and 72° C. for 1 minute in the given order, then to 35-time cycles of incubating at 94° C. for 1 minute, 64° C. for 1 minute and 72° C. for 1 minute in the given order to effect PCR reaction, thus obtaining a DNA fragment which consisted of the nucleotide sequence of SEQ ID NO:5, a digestion site for restriction enzyme SalI and a Kozak's sequence both linked to the 5'-terminal of the nucleotide sequence of SEQ ID NO:5, and a digestion site for restriction enzyme NotI and a nucleotide sequence encoding $(His)_6$ tag both linked to the 3'-terminal of the nucleotide sequence of SEQ ID NO:5. This DNA fragment was introduced similarly as in Example 6-1 in "XL1-Blue MRFKan", a strain of Escherichia coli commercialized by Stratagene Cloning Systems, California, U.S.A., to obtain a transformant which contained a recombinant DNA "pEFHIL18RD1-2-H" according to this invention. Analysis of the recombinant DNA in usual manner confirmed that in this recombinant DNA a cDNA "HIL18RD1-2-H", which contained the nucleotide sequence of SEQ ID NO:5 encoding the polypeptide of this invention, was located downstream the elongation factor promotor EF1αP as shown in FIG. 8.

The recombinant DNA "pEFHIL18RD1-2-H" was introduced in COS-1 cells similarly as in Example 6-2 using the transformant thus obtained, and the COS-1 cells were then cultivated similarly as in Example 6-3. The supernatant of the resultant culture was concentrated with membrane filtration, and charged on a column of "Ni-NTA Spin Kit", a gel product for affinity chromatography commercialized by QIAGEN GmbH, Hilden, Germany, which was then applied with PBS containing 20 mM imidazole to remove the non-adsorbed fractions. Thereafter, the column was applied with PBS containing 250 mM imidazole, and the eluate was collected in fractions while checking the presence of human soluble polypeptide in each fraction by the method in Example 1-1 using $^{125}$I-labelled human IL-18, after which the fractions with the polypeptide were collected and pooled, thus obtaining about 2 ml of an aqueous solution containing the polypeptide with the amino acid sequence of SEQ ID NO:23 per starting $10^8$ cells. The protein content in the solution was about 10 μg/ml.

The soluble polypeptide thus obtained was studied for physicochemical properties by the method in Example 1. As the result, the soluble polypeptide obtained in this Example contained a part or whole of each amino acid sequences in SEQ ID NOs:14 to 16 and 19 as partial amino acid sequences, as well as exhibiting physiological activities which were similar to those of IL-18R from L428 cell.

EXAMPLE 8

Soluble Polypeptide of Human Origin

Figure 9:
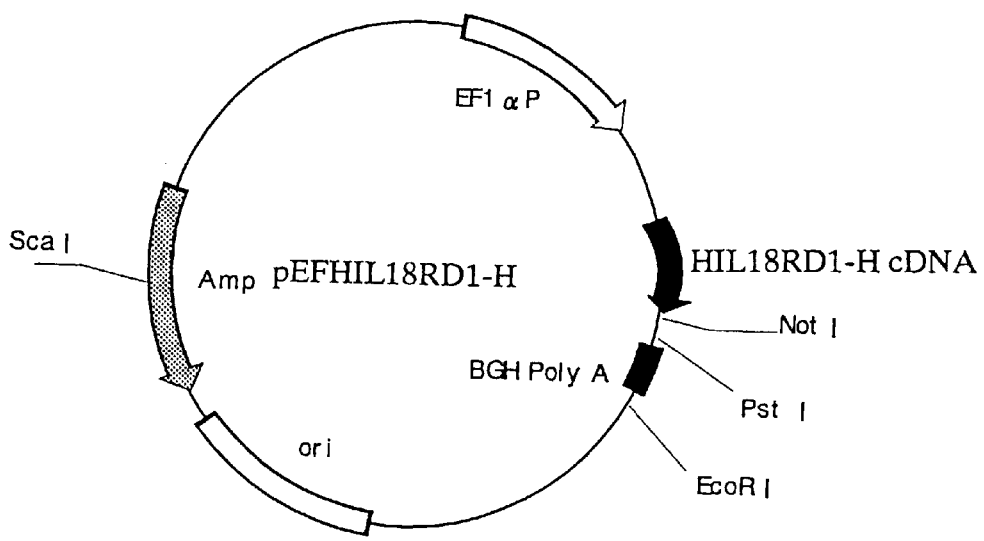
FIG. 9 shows the structure of the recombinant DNA "pEFHIL18RD1-H" of this invention.
Figure 10:
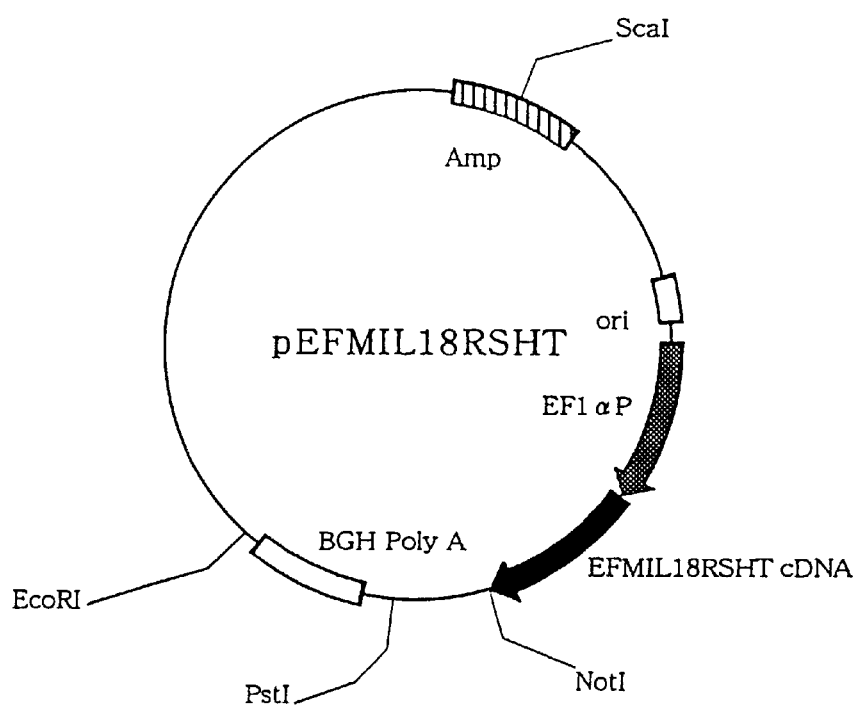
FIG. 10 shows the structure of the recombinant DNA "pEFMIL18RSHT" of this invention.

A transformant containing a recombinant DNA "pEFHIL18RD1-H" according to this invention was prepared similarly as in Example 7, except that sense and antisense primers were replaced with oligonucleotides having respective nucleotide sequences as shown with 5'-TCAGTCGACGCCACCATGAATTGTAGAG-3' (SEQ ID NO:34) and 5'-GAAGCGGCCGCTCATTAGTGATGGTGATGGTG ATGTCTTTCAGTGAAACAGCT-3' (SEQ ID NO:35). Analysis of the recombinant DNA in usual manner confirmed that in the recombinant DNA a cDNA "HIL18RD1-H", which contained the nucleotide sequence of SEQ ID NO:3 encoding the polypeptide of this invention, was located downstream the elongation factor promotor EF1αP as shown in FIG. 9. Thereafter, similarly as in Example 7, the recombinant DNA was introduced in COS-1 cells and brought into expression, thus obtaining about 2 ml of an aqueous solution containing a polypeptide with the amino acid sequence of SEQ ID NO:24 per $10^8$ starting cells. The protein content in the solution was about 10 μg/ml.

The polypeptide of this invention thus obtained were studied for physicochemical properties by the method in Example 1. As the result, the soluble polypeptide obtained in this Example contained each amino acid sequences of SEQ ID NOs:14 and 15 as partial amino acid sequences, as well as exhibiting physiological activities which were similar to those of the IL-18R from L428 cell.

EXAMPLE 9

Soluble Polypeptide of Mouse Origin

EXAMPLE 9-1

Preparation of Recombinant DNA

A reaction product containing a first strand cDNA was obtained by subjecting an mRNA, prepared in usual manner from mouse liver, in place with that from L428 cell to the same reaction to synthesize first strand cDNA as in Example 2-3. The reaction product was treated by the same PCR method as in Example 2-3, except that the sense and antisense primers were replaced with oligonucleotides having respective nucleotide sequence as shown with 5'-TCAGTCGACGCCACCATGCATCATGAAGAA-3' (SEQ ID NO:36) and 5'-GAAGCGGCCGCATCATTAGTGATGGTGATGG TGATGTGTAAAGACATGGCC-3' (SEQ ID NO:37), which had been prepared on the basis of the amino acid sequence described in P. Parnet et al., *The Journal of Biological Chemistry*, Vol.271, pp.3,967–3,970 (1996) and also the nucleotide sequence of SEQ ID NO:1: This operation gave a DNA fragment which comprised the nucleotide sequence of SEQ ID NO:11, a digestion site for restriction enzyme SalI linked to the 5'-terminal in the nucleotide sequence of the SEQ ID NO:11, and a cleavage site for restriction enzyme NotI and a nucleotide sequence encoding $(His)_6$ tag both linked to the 3'-terminal in the nucleotide sequence of the SEQ ID NO:11.

According to the method in Example 6-1, this DNA fragment was introduced into "XL1-BLUE MRFKAN", a strain of Escherichia coli commercialized by Stratagene Cloning Systems, California, U.S.A., to transform. After a plasmid DNA was collected from the transformant and confirmed to contain the nucleotide sequence of SEQ ID NO:11, the plasmid DNA was introduced into "XL1-BLUE MRFKAN", a strain of Escherichia coli strain commercialized by Stratagene Cloning Systems, California, U.S.A., to obtain a transformant "EFMIL18RSHT" which contains a recombinant DNA "pEFMIL18RSHT" according to this invention. Analysis in usual manner confirmed that in the recombinant DNA "pEFMIL18RSHT" a cDNA "EFMIL18RSHT cDNA", which contained the nucleotide sequence of SEQ ID NO:4 encoding the polypeptide of this invention, was linked to downstream of the elongation factor 1 promotor EF1αP, as shown in FIG. 8.

EXAMPLE 9-2

Preparation of Transformant and Soluble Polypeptide

According to the method in Example 6-2, a plasmid DNA was collected from a transformant "EFMIL18RSHT"

obtained by the method in Example 9-1, and introduced into COS-1 cells to obtain transformant cells which contained a DNA encoding a soluble polypeptide of mouse origin.

"ASF104", a serum-free nutrient culture medium commercialized by Ajinomoto Co., Inc., Tokyo, Japan, was distributed in flat-bottomed culture bottles, inoculated with the transformed COS-1 cells to give a cell density of $1\times10^5$ cells/ml, and cultivated in usual manner at 37° C. in 5 v/v % $CO_2$ incubator for 3 days. The supernatant was collected from the resultant culture and charged to a column of "Ni-NTA", a gel product for affinity chromatography, commercialized by QIAGEN GmbH, Hilden, Germany, after which the column was applied first with PBS containing 20 mM imidazole to remove non-adsorbed components, then with PBS containing 250 mM imidazole while collecting and fractionating the eluate. The fractions were checked for presence of mouse soluble polypeptide by the method in Example 1-1 using $^{125}$I-labelled mouse IL-18, selected and pooled, thus obtaining per 108 starting cells about 2 ml of an aqueous solution which contained a polypeptide with the amino acid sequence of SEQ ID NO:25. The protein content in the solution was about 100 µg/ml. The soluble polypeptide thus obtained was studied in accordance with the method in Example 1, revealing that it efficiently neutralized mouse IL-18.

EXAMPLE 10

Liquid Agent

Either polypeptide obtained by the method in Examples 5 to 8 was separately dissolved in aliquots of physiological saline containing as stabilizer 1 w/v % "TREHAOSE", a powdered crystalline trehalose commercialized by Hayashibara Co., Ltd., Okayama, Japan, to give respective concentration of 1 mg/ml, and the resultant mixtures were separately and sterilely filtered with membrane in usual manner to obtain four distinct liquid agents.

The products, which are excellent in stability, are useful as injection, ophthalmic solution and collunarium in treatment and prevention of susceptive diseases including autoimmune diseases.

EXAMPLE 11

Dried Injection

One hundred milligrams of either polypeptide obtained by the methods in Example 5 to 8 was separately dissolved in aliquots of physiological saline containing 1 w/v % sucrose as stabilizer, the resultant solutions were separately and sterilely filtered with membrane, distributed in vials in every 1 ml aliquot, lyophilized and sealed in usual manner to obtain four distinct pulverized agents.

The products, which are excellent in stability, are useful as dried injection in treatment and prevention of susceptive diseases including autoimmune diseases.

EXAMPLE 12

Ointment

"HI-BIS-WAKO 104", a carboxyvinylpolymer commercialized by Wako Pure Chemicals, Tokyo, Japan, and "TREHAOSE", a powdered crystalline trehalose commercialized by Hayashibara Co., Ltd., Okayama, Japan, were dissolved in sterilized distilled water to give respective concentrations of 1.4 w/w % and 2.0 w/w %, and either polypeptide obtained by the methods in Examples 5 to 8 was separately mixed with aliquots of the resultant solution to homogeneity, and adjusted to pH7.2 to obtain four distinct paste agents containing about 1 mg/g of the polypeptide of this invention each.

The products, which are excellent in both spreadablity and stability, are useful as ointment in treatment and prevention of susceptive diseases including autoimmune diseases.

EXAMPLE 13

Tablet

Aliquots of "FINETOSE", a pulverized anhydrous crystalline alpha-maltose commercialized by Hayashibara Co., Ltd., Okayama, Japan, were separately admixed with either polypeptide, obtained by the methods in Examples 5 to 8, and aliquots of "LUMIN" as cell activator, [bis-4-(1-ethylquinoline)][γ-4'-(1-ethylquinoline)] pentamethionine cyanine, to homogeneity, and the resultant mixtures were separately tableted in usual manner to obtain four distinct types of tablets, about 200 mg each, containing about 1mg/tablet of the polypeptide of this invention and also 1 mg/tablet of LUMIN each.

The products, which are excellent in swallowability and stability and also bears an cell activating property, are useful as tablet in treatment and prevention of susceptive diseases including autoimmune diseases.

Experiment

Acute Toxicity Test

In usual manner, a variety of agents, obtained by the methods in Examples 10 to 13, were percutaneously or orally administrated or intraperitoneally injected to 8 week-old mice. As the result, the $LD_{50}$ of each sample was proved about 1 mg or higher per body weight of mouse in terms of the amount of the polypeptide, regardless of administration route. This does support that the polypeptide of this invention is safe when incorporated in pharmaceuticals directed to use in mammals including human.

As explained above, this invention is based on the discovery of a novel receptor protein which recognizes IL-18. The polypeptide of this invention exhibits a remarkable efficacy in relief of rejection reaction associated with grafts of organs and also in treatment and prevention of various disease resulting from excessive immunoreaction because the polypeptide bears properties of suppressing and regulating immunoreaction in mammals including human. Further, the polypeptide of this invention is useful in clarification of physiological activities of IL-18, establishment of hybridoma cells which are capable of producing monoclonal antibodies specific to IL-18R, and also affinity chromatography and labelled assay to purify and detect IL-18. In addition, the polypeptide of this invention, in particular, that in soluble form is useful in screening in vivo and in vitro agonists and antagonists to IL-18. The polypeptide of this invention, which bears these outstanding usefulness, can be easily prepared in desired amounts by the process according to this invention using recombinant DNA techniques.

This invention, which exhibits these remarkable effects, would be very significant and contributive to the art.

What is claimed is:

1. An isolated DNA comprising a nucleotide sequence encoding an interleukin-18 (IL-18) binding polypeptide which is capable of binding interleukin-18 (IL-18), wherein said nucleotide sequence is selected from the group consisting of SEQ ID NO:1, SEQ ID NO:6, SEQ ID NO:7, SEQ ID NO:10, and complementary sequence thereto.

2. The isolated DNA according to claim 1, wherein, based on the degeneracy of the genetic code, one or more nucleotides are replaced with different nucleotides while conserving the amino acid sequence.

3. An autonomously replicable vector, comprising the isolated DNA according to claim 1.

4. A host cell of animal, plant or microbial origin transformed with the isolated DNA of claim 1.

5. A process for preparing an interleukin-18 (IL-18) binding polypeptide which is capable of binding interleukin-18 (IL-18) and which comprises a fragment of interleukin-18 (IL-18) receptor, comprising:

culturing a transformed host cell to express and produce said interleukin-18 (IL-18) binding polypeptide encoded by the isolated DNA of claim 1;

and collecting the resultant produced IL-18 binding polypeptide.

6. The process according to claim 5 wherein the resultant IL-18 binding polypeptide is collected by one or more techniques selected from the group consisting of salting out, dialysis, filtration, concentration, fractional precipitation, ion-exchange chromatography, gel filtration chromatography, adsorption chromatography, isoelectric focussing chromatography, hydrophobic chromatography, reversed phase chromatography, affinity chromatography, gel electrophoresis, and isoelectric focussing gelelectrophoresis.

7. The process according to claim 5, wherein the resultant polypeptide is collected through a step which includes immunoaffinity chromatography using monoclonal antibody.

8. The isolated DNA according to claim 1, wherein said interleukin-18 (IL-18) binding polypeptide comprises the amino acid sequence of SEQ ID NO:20.

* * * * *

SEQUENCE LISTING (1) GENERAL INFORMATION:

(iii) NUMBER OF SEQUENCES: 37

(2) INFORMATION FOR SEQ ID NO: 1:

(i) SEQUENCE CHARACTERISTICS:
       (A) LENGTH: 1563 base pairs
       (B) TYPE: nucleic acid
       (C) STRANDEDNESS: double
       (D) TOPOLOGY: linear (ii) MOLECULE TYPE: cDNA (ix) FEATURE:
       (A) NAME/KEY:mat peptide
       (B) LOCATION:1..1563
       (C) IDENTIFICATION METHOD:E (xi) SEQUENCE DESCRIPTION: SEQ ID NO: 1:

```
GAA TCT TGT ACT TCA CGT CCC CAC ATT ACT GTG GTT GAA GGG GAA CCT      48
Glu Ser Cys Thr Ser Arg Pro His Ile Thr Val Val Glu Gly Glu Pro
 1               5                  10                  15

TTC TAT CTG AAA CAT TGC TCG TGT TCA CTT GCA CAT GAG ATT GAA ACA      96
Phe Tyr Leu Lys His Cys Ser Cys Ser Leu Ala His Glu Ile Glu Thr
             20                  25                  30

ACC ACC AAA AGC TGG TAC AAA AGC AGT GGA TCA CAG GAA CAT GTG GAG     144
Thr Thr Lys Ser Trp Tyr Lys Ser Ser Gly Ser Gln Glu His Val Glu
         35                  40                  45

CTG AAC CCA AGG AGT TCC TCG AGA ATT GCT TTG CAT GAT TGT GTT TTG     192
Leu Asn Pro Arg Ser Ser Ser Arg Ile Ala Leu His Asp Cys Val Leu
     50                  55                  60

GAG TTT TGG CCA GTT GAG TTG AAT GAC ACA GGA TCT TAC TTT TTC CAA     240
Glu Phe Trp Pro Val Glu Leu Asn Asp Thr Gly Ser Tyr Phe Phe Gln
 65                  70                  75                  80

ATG AAA AAT TAT ACT CAG AAA TGG AAA TTA AAT GTC ATC AGA AGA AAT     288
Met Lys Asn Tyr Thr Gln Lys Trp Lys Leu Asn Val Ile Arg Arg Asn
                 85                  90                  95

AAA CAC AGC TGT TTC ACT GAA AGA CAA GTA ACT AGT AAA ATT GTG GAA     336
Lys His Ser Cys Phe Thr Glu Arg Gln Val Thr Ser Lys Ile Val Glu
            100                 105                 110

GTT AAA AAA TTT TTT CAG ATA ACC TGT GAA AAC AGT TAC TAT CAA ACA     384
Val Lys Lys Phe Phe Gln Ile Thr Cys Glu Asn Ser Tyr Tyr Gln Thr
        115                 120                 125

CTG GTC AAC AGC ACA TCA TTG TAT AAG AAC TGT AAA AAG CTA CTA CTG     432
Leu Val Asn Ser Thr Ser Leu Tyr Lys Asn Cys Lys Lys Leu Leu Leu
    130                 135                 140

GAG AAC AAT AAA AAC CCA ACG ATA AAG AAG AAC GCC GAG TTT GAA GAT     480
Glu Asn Asn Lys Asn Pro Thr Ile Lys Lys Asn Ala Glu Phe Glu Asp
145                 150                 155                 160

CAG GGG TAT TAC TCC TGC GTG CAT TTC CTT CAT CAT AAT GGA AAA CTA     528
Gln Gly Tyr Tyr Ser Cys Val His Phe Leu His His Asn Gly Lys Leu
                165                 170                 175

TTT AAT ATC ACC AAA ACC TTC AAT ATA ACA ATA GTG GAA GAT CGC AGT     576
Phe Asn Ile Thr Lys Thr Phe Asn Ile Thr Ile Val Glu Asp Arg Ser
            180                 185                 190

AAT ATA GTT CCG GTT CTT CTT GGA CCA AAG CTT AAC CAT GTT GCA GTG     624
Asn Ile Val Pro Val Leu Leu Gly Pro Lys Leu Asn His Val Ala Val
        195                 200                 205

GAA TTA GGA AAA AAC GTA AGG CTC AAC TGC TCT GCT TTG CTG AAT GAA     672
Glu Leu Gly Lys Asn Val Arg Leu Asn Cys Ser Ala Leu Leu Asn Glu
```

```
                210                     215                     220
GAG GAT GTA ATT TAT TGG ATG TTC GGG GAA GAA AAT GGA TCG GAT CCT        720
Glu Asp Val Ile Tyr Trp Met Phe Gly Glu Glu Asn Gly Ser Asp Pro
225                     230                     235                 240

AAT ATA CAT GAA GAG AAA GAA ATG AGA ATT ATG ACT CCA GAA GGC AAA        768
Asn Ile His Glu Glu Lys Glu Met Arg Ile Met Thr Pro Glu Gly Lys
                    245                     250                     255

TGG CAT GCT TCA AAA GTA TTG AGA ATT GAA AAT ATT GGT GAA AGC AAT        816
Trp His Ala Ser Lys Val Leu Arg Ile Glu Asn Ile Gly Glu Ser Asn
                260                     265                     270

CTA AAT GTT TTA TAT AAT TGC ACT GTG GCC AGC ACG GGA GGC ACA GAC        864
Leu Asn Val Leu Tyr Asn Cys Thr Val Ala Ser Thr Gly Gly Thr Asp
            275                     280                     285

ACC AAA AGC TTC ATC TTG GTG AGA AAA GAC ATG GCT GAT ATC CCA GGC        912
Thr Lys Ser Phe Ile Leu Val Arg Lys Asp Met Ala Asp Ile Pro Gly
        290                     295                     300

CAC GTC TTC ACA AGA GGA ATG ATC ATA GCT GTT TTG ATC TTG GTG GCA        960
His Val Phe Thr Arg Gly Met Ile Ile Ala Val Leu Ile Leu Val Ala
305                     310                     315                 320

GTA GTG TGC CTA GTG ACT GTG TGT GTC ATT TAT AGA GTT GAC TTG GTT       1008
Val Val Cys Leu Val Thr Val Cys Val Ile Tyr Arg Val Asp Leu Val
                    325                     330                     335

CTA TTT TAT AGA CAT TTA ACG AGA AGA GAT GAA ACA TTA ACA GAT GGA       1056
Leu Phe Tyr Arg His Leu Thr Arg Arg Asp Glu Thr Leu Thr Asp Gly
                340                     345                     350

AAA ACA TAT GAT GCT TTT GTG TCT TAC CTA AAA GAA TGC CGA CCT GAA       1104
Lys Thr Tyr Asp Ala Phe Val Ser Tyr Leu Lys Glu Cys Arg Pro Glu
            355                     360                     365

AAT GGA GAG GAG CAC ACC TTT GCT GTG GAG ATT TTG CCC AGG GTG TTG       1152
Asn Gly Glu Glu His Thr Phe Ala Val Glu Ile Leu Pro Arg Val Leu
        370                     375                     380

GAG AAA CAT TTT GGG TAT AAG TTA TGC ATA TTT GAA AGG GAT GTA GTG       1200
Glu Lys His Phe Gly Tyr Lys Leu Cys Ile Phe Glu Arg Asp Val Val
385                     390                     395                 400

CCT GGA GGA GCT GTT GTT GAT GAA ATC CAC TCA CTG ATA GAG AAA AGC       1248
Pro Gly Gly Ala Val Val Asp Glu Ile His Ser Leu Ile Glu Lys Ser
                    405                     410                     415

CGA AGA CTA ATC ATT GTC CTA AGT AAA AGT TAT ATG TCT AAT GAG GTC       1296
Arg Arg Leu Ile Ile Val Leu Ser Lys Ser Tyr Met Ser Asn Glu Val
                420                     425                     430

AGG TAT GAA CTT GAA AGT GGA CTC CAT GAA GCA TTG GTG GAA AGA AAA       1344
Arg Tyr Glu Leu Glu Ser Gly Leu His Glu Ala Leu Val Glu Arg Lys
            435                     440                     445

ATT AAA ATA ATC TTA ATT GAA TTT ACA CCT GTT ACT GAC TTC ACA TTC       1392
Ile Lys Ile Ile Leu Ile Glu Phe Thr Pro Val Thr Asp Phe Thr Phe
        450                     455                     460

TTG CCC CAA TCA CTA AAG CTT TTG AAA TCT CAC AGA GTT CTG AAG TGG       1440
Leu Pro Gln Ser Leu Lys Leu Leu Lys Ser His Arg Val Leu Lys Trp
465                     470                     475                 480

AAG GCC GAT AAA TCT CTT TCT TAT AAC TCA AGG TTC TGG AAG AAC CTT       1488
Lys Ala Asp Lys Ser Leu Ser Tyr Asn Ser Arg Phe Trp Lys Asn Leu
                    485                     490                     495

CTT TAC TTA ATG CCT GCA AAA ACA GTC AAG CCA GGT AGA GAC GAA CCG       1536
Leu Tyr Leu Met Pro Ala Lys Thr Val Lys Pro Gly Arg Asp Glu Pro
                500                     505                     510

GAA GTC TTG CCT GTT CTT TCC GAG TCT                                   1563
Glu Val Leu Pro Val Leu Ser Glu Ser
            515                     520
```

(2) INFORMATION FOR SEQ ID NO: 2:

(i) SEQUENCE CHARACTERISTICS:
        (A) LENGTH: 1557 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY:mat peptide
        (B) LOCATION:1..1557
        (C) IDENTIFICATION METHOD:S (xi) SEQUENCE DESCRIPTION: SEQ ID NO: 2:

```
TCA AAA AGT TGT ATT CAC CGA TCA CAA ATT CAT GTG GTA GAG GGA GAA      48
Ser Lys Ser Cys Ile His Arg Ser Gln Ile His Val Val Glu Gly Glu
 1               5                  10                  15

CCT TTT TAT CTG AAG CCA TGT GGC ATA TCT GCA CCA GTG CAC AGG AAT      96
Pro Phe Tyr Leu Lys Pro Cys Gly Ile Ser Ala Pro Val His Arg Asn
            20                  25                  30

GAA ACA GCC ACC ATG AGA TGG TTC AAA GGC AGT GCT TCA CAT GAG TAT     144
Glu Thr Ala Thr Met Arg Trp Phe Lys Gly Ser Ala Ser His Glu Tyr
        35                  40                  45

AGA GAG CTG AAC AAC AGA AGC TCG CCC AGA GTC ACT TTT CAT GAT CAC     192
Arg Glu Leu Asn Asn Arg Ser Ser Pro Arg Val Thr Phe His Asp His
 50                  55                  60

ACC TTG GAA TTC TGG CCA GTT GAG ATG GAG GAT GAG GGA ACG TAC ATT     240
Thr Leu Glu Phe Trp Pro Val Glu Met Glu Asp Glu Gly Thr Tyr Ile
 65                  70                  75                  80

TCT CAA GTC GGA AAT GAT CGT CGC AAT TGG ACC TTA AAT GTC ACC AAA     288
Ser Gln Val Gly Asn Asp Arg Arg Asn Trp Thr Leu Asn Val Thr Lys
            85                  90                  95

AGA AAC AAA CAC AGC TGT TTC TCT GAC AAG CTC GTG ACA AGC AGA GAT     336
Arg Asn Lys His Ser Cys Phe Ser Asp Lys Leu Val Thr Ser Arg Asp
            100                 105                 110

GTT GAA GTT AAC AAA TCT CTG CAT ATC ACT TGT AAG AAT CCT AAC TAT     384
Val Glu Val Asn Lys Ser Leu His Ile Thr Cys Lys Asn Pro Asn Tyr
        115                 120                 125

GAA GAG CTG ATC CAG GAC ACA TGG CTG TAT AAG AAC TGT AAG GAA ATA     432
Glu Glu Leu Ile Gln Asp Thr Trp Leu Tyr Lys Asn Cys Lys Glu Ile
130                 135                 140

TCC AAA ACC CCA AGG ATC CTG AAG GAT GCC GAG TTT GGA GAT GAG GGC     480
Ser Lys Thr Pro Arg Ile Leu Lys Asp Ala Glu Phe Gly Asp Glu Gly
145                 150                 155                 160

TAC TAC TCC TGC GTG TTT TCT GTC CAC CAT AAT GGG ACA CGG TAC AAC     528
Tyr Tyr Ser Cys Val Phe Ser Val His His Asn Gly Thr Arg Tyr Asn
                165                 170                 175

ATC ACC AAG ACT GTC AAT ATA ACA GTT ATT GAA GGA AGG AGT AAA GTA     576
Ile Thr Lys Thr Val Asn Ile Thr Val Ile Glu Gly Arg Ser Lys Val
            180                 185                 190

ACT CCA GCT ATT TTA GGA CCA AAG TGT GAG AAG GTT GGT GTA GAA CTA     624
Thr Pro Ala Ile Leu Gly Pro Lys Cys Glu Lys Val Gly Val Glu Leu
            195                 200                 205

GGA AAG GAT GTG GAG TTG AAC TGC AGT GCT TCA TTG AAT AAA GAC GAT     672
Gly Lys Asp Val Glu Leu Asn Cys Ser Ala Ser Leu Asn Lys Asp Asp
210                 215                 220

CTG TTT TAT TGG AGC ATC AGG AAA GAG GAC AGC TCA GAC CCT AAT GTG     720
Leu Phe Tyr Trp Ser Ile Arg Lys Glu Asp Ser Ser Asp Pro Asn Val
225                 230                 235                 240

CAA GAA GAC AGG AAG GAG ACG ACA ACA TGG ATT TCT GAA GGC AAA CTG     768
Gln Glu Asp Arg Lys Glu Thr Thr Thr Trp Ile Ser Glu Gly Lys Leu
```

```
                    245                 250                 255
CAT GCT TCA AAA ATA CTG AGA TTT CAG AAA ATT ACT GAA AAC TAT CTC    816
His Ala Ser Lys Ile Leu Arg Phe Gln Lys Ile Thr Glu Asn Tyr Leu
            260                 265                 270

AAT GTT TTA TAT AAT TGC ACC GTG GCC AAC GAA GAA GCC ATA GAC ACC    864
Asn Val Leu Tyr Asn Cys Thr Val Ala Asn Glu Glu Ala Ile Asp Thr
            275                 280                 285

AAG AGC TTC GTC TTG GTG AGA AAA GAA ATA CCT GAT ATC CCA GGC CAT    912
Lys Ser Phe Val Leu Val Arg Lys Glu Ile Pro Asp Ile Pro Gly His
        290                 295                 300

GTC TTT ACA GGA GGA GTA ACT GTG CTT GTT CTC GCC TCT GTG GCA GCA    960
Val Phe Thr Gly Gly Val Thr Val Leu Val Leu Ala Ser Val Ala Ala
305                 310                 315                 320

GTG TGT ATA GTG ATT TTG TGT GTC ATT TAT AAA GTT GAC TTG GTT CTG   1008
Val Cys Ile Val Ile Leu Cys Val Ile Tyr Lys Val Asp Leu Val Leu
                325                 330                 335

TTC TAT AGG CGC ATA GCG GAA AGA GAC GAG ACA CTA ACA GAT GGT AAA   1056
Phe Tyr Arg Arg Ile Ala Glu Arg Asp Glu Thr Leu Thr Asp Gly Lys
            340                 345                 350

ACA TAT GAT GCC TTT GTG TCT TAC CTG AAA GAG TGT CAT CCT GAG AAT   1104
Thr Tyr Asp Ala Phe Val Ser Tyr Leu Lys Glu Cys His Pro Glu Asn
            355                 360                 365

AAA GAA GAG TAT ACT TTT GCT GTG GAG ACG TTA CCC AGG GTC CTG GAG   1152
Lys Glu Glu Tyr Thr Phe Ala Val Glu Thr Leu Pro Arg Val Leu Glu
        370                 375                 380

AAA CAG TTT GGG TAT AAG TTA TGC ATA TTT GAA AGA GAT GTG GTG CCT   1200
Lys Gln Phe Gly Tyr Lys Leu Cys Ile Phe Glu Arg Asp Val Val Pro
385                 390                 395                 400

GGC GGA GCT GTT GTC GAG GAG ATC CAT TCA CTG ATA GAG AAA AGC CGG   1248
Gly Gly Ala Val Val Glu Glu Ile His Ser Leu Ile Glu Lys Ser Arg
                405                 410                 415

AGG CTA ATC ATC GTT CTC AGC CAG AGT TAC CTG ACT AAC GGA GCC AGG   1296
Arg Leu Ile Ile Val Leu Ser Gln Ser Tyr Leu Thr Asn Gly Ala Arg
            420                 425                 430

CGT GAG CTC GAG AGT GGA CTC CAC GAA GCA CTG GTA GAG AGG AAG ATT   1344
Arg Glu Leu Glu Ser Gly Leu His Glu Ala Leu Val Glu Arg Lys Ile
            435                 440                 445

AAG ATC ATC TTA ATT GAG TTT ACT CCA GCC AGC AAC ATC ACC TTT CTC   1392
Lys Ile Ile Leu Ile Glu Phe Thr Pro Ala Ser Asn Ile Thr Phe Leu
450                 455                 460

CCC CCG TCG CTG AAA CTC CTG AAG TCC TAC AGA GTT CTA AAA TGG AGG   1440
Pro Pro Ser Leu Lys Leu Leu Lys Ser Tyr Arg Val Leu Lys Trp Arg
465                 470                 475                 480

GCT GAC AGT CCC TCC ATG AAC TCA AGG TTC TGG AAG AAT CTT GTT TAC   1488
Ala Asp Ser Pro Ser Met Asn Ser Arg Phe Trp Lys Asn Leu Val Tyr
                485                 490                 495

CTG ATG CCC GCA AAA GCC GTC AAG CCA TGG AGA GAG GAG TCG GAG GCG   1536
Leu Met Pro Ala Lys Ala Val Lys Pro Trp Arg Glu Glu Ser Glu Ala
            500                 505                 510

CGG TCT GTT CTC TCA GCA CCT                                       1557
Arg Ser Val Leu Ser Ala Pro
        515
```

(2) INFORMATION FOR SEQ ID NO: 3:

(i) SEQUENCE CHARACTERISTICS:
        (A) LENGTH: 312 base pairs
        (B) TYPE: nucleic acid
        (C) STRANDEDNESS: double
        (D) TOPOLOGY: linear (ii) MOLECULE TYPE: cDNA (ix) FEATURE:
    (A) NAME/KEY:mat peptide
    (B) LOCATION:1..312
    (C) IDENTIFICATION METHOD:S (xi) SEQUENCE DESCRIPTION: SEQ ID NO: 3:

```
GAA TCT TGT ACT TCA CGT CCC CAC ATT ACT GTG GTT GAA GGG GAA CCT      48
Glu Ser Cys Thr Ser Arg Pro His Ile Thr Val Val Glu Gly Glu Pro
 1               5                  10                  15

TTC TAT CTG AAA CAT TGC TCG TGT TCA CTT GCA CAT GAG ATT GAA ACA      96
Phe Tyr Leu Lys His Cys Ser Cys Ser Leu Ala His Glu Ile Glu Thr
            20                  25                  30

ACC ACC AAA AGC TGG TAC AAA AGC AGT GGA TCA CAG GAA CAT GTG GAG     144
Thr Thr Lys Ser Trp Tyr Lys Ser Ser Gly Ser Gln Glu His Val Glu
        35                  40                  45

CTG AAC CCA AGG AGT TCC TCG AGA ATT GCT TTG CAT GAT TGT GTT TTG     192
Leu Asn Pro Arg Ser Ser Ser Arg Ile Ala Leu His Asp Cys Val Leu
    50                  55                  60

GAG TTT TGG CCA GTT GAG TTG AAT GAC ACA GGA TCT TAC TTT TTC CAA     240
Glu Phe Trp Pro Val Glu Leu Asn Asp Thr Gly Ser Tyr Phe Phe Gln
65                  70                  75                  80

ATG AAA AAT TAT ACT CAG AAA TGG AAA TTA AAT GTC ATC AGA AGA AAT     288
Met Lys Asn Tyr Thr Gln Lys Trp Lys Leu Asn Val Ile Arg Arg Asn
                85                  90                  95

AAA CAC AGC TGT TTC ACT GAA AGA                                     312
Lys His Ser Cys Phe Thr Glu Arg
                100
```

(2) INFORMATION FOR SEQ ID NO: 4:

(i) SEQUENCE CHARACTERISTICS:
        (A) LENGTH: 921 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY:mat peptide
        (B) LOCATION:1..921
        (C) IDENTIFICATION METHOD:S (xi) SEQUENCE DESCRIPTION: SEQ ID NO: 4:

```
TCA AAA AGT TGT ATT CAC CGA TCA CAA ATT CAT GTG GTA GAG GGA GAA      48
Ser Lys Ser Cys Ile His Arg Ser Gln Ile His Val Val Glu Gly Glu
 1               5                  10                  15

CCT TTT TAT CTG AAG CCA TGT GGC ATA TCT GCA CCA GTG CAC AGG AAT      96
Pro Phe Tyr Leu Lys Pro Cys Gly Ile Ser Ala Pro Val His Arg Asn
            20                  25                  30

GAA ACA GCC ACC ATG AGA TGG TTC AAA GGC AGT GCT TCA CAT GAG TAT     144
Glu Thr Ala Thr Met Arg Trp Phe Lys Gly Ser Ala Ser His Glu Tyr
        35                  40                  45

AGA GAG CTG AAC AAC AGA AGC TCG CCC AGA GTC ACT TTT CAT GAT CAC     192
Arg Glu Leu Asn Asn Arg Ser Ser Pro Arg Val Thr Phe His Asp His
    50                  55                  60

ACC TTG GAA TTC TGG CCA GTT GAG ATG GAG GAT GAG GGA ACG TAC ATT     240
Thr Leu Glu Phe Trp Pro Val Glu Met Glu Asp Glu Gly Thr Tyr Ile
65                  70                  75                  80

TCT CAA GTC GGA AAT GAT CGT CGC AAT TGG ACC TTA AAT GTC ACC AAA     288
Ser Gln Val Gly Asn Asp Arg Arg Asn Trp Thr Leu Asn Val Thr Lys
                85                  90                  95
```

```
AGA AAC AAA CAC AGC TGT TTC TCT GAC AAG CTC GTG ACA AGC AGA GAT        336
Arg Asn Lys His Ser Cys Phe Ser Asp Lys Leu Val Thr Ser Arg Asp
            100                 105                 110

GTT GAA GTT AAC AAA TCT CTG CAT ATC ACT TGT AAG AAT CCT AAC TAT        384
Val Glu Val Asn Lys Ser Leu His Ile Thr Cys Lys Asn Pro Asn Tyr
            115                 120                 125

GAA GAG CTG ATC CAG GAC ACA TGG CTG TAT AAG AAC TGT AAG GAA ATA        432
Glu Glu Leu Ile Gln Asp Thr Trp Leu Tyr Lys Asn Cys Lys Glu Ile
        130                 135                 140

TCC AAA ACC CCA AGG ATC CTG AAG GAT GCC GAG TTT GGA GAT GAG GGC        480
Ser Lys Thr Pro Arg Ile Leu Lys Asp Ala Glu Phe Gly Asp Glu Gly
145                 150                 155                 160

TAC TAC TCC TGC GTG TTT TCT GTC CAC CAT AAT GGG ACA CGG TAC AAC        528
Tyr Tyr Ser Cys Val Phe Ser Val His His Asn Gly Thr Arg Tyr Asn
                165                 170                 175

ATC ACC AAG ACT GTC AAT ATA ACA GTT ATT GAA GGA AGG AGT AAA GTA        576
Ile Thr Lys Thr Val Asn Ile Thr Val Ile Glu Gly Arg Ser Lys Val
            180                 185                 190

ACT CCA GCT ATT TTA GGA CCA AAG TGT GAG AAG GTT GGT GTA GAA CTA        624
Thr Pro Ala Ile Leu Gly Pro Lys Cys Glu Lys Val Gly Val Glu Leu
        195                 200                 205

GGA AAG GAT GTG GAG TTG AAC TGC AGT GCT TCA TTG AAT AAA GAC GAT        672
Gly Lys Asp Val Glu Leu Asn Cys Ser Ala Ser Leu Asn Lys Asp Asp
210                 215                 220

CTG TTT TAT TGG AGC ATC AGG AAA GAG GAC AGC TCA GAC CCT AAT GTG        720
Leu Phe Tyr Trp Ser Ile Arg Lys Glu Asp Ser Ser Asp Pro Asn Val
225                 230                 235                 240

CAA GAA GAC AGG AAG GAG ACG ACA ACA TGG ATT TCT GAA GGC AAA CTG        768
Gln Glu Asp Arg Lys Glu Thr Thr Thr Trp Ile Ser Glu Gly Lys Leu
                245                 250                 255

CAT GCT TCA AAA ATA CTG AGA TTT CAG AAA ATT ACT GAA AAC TAT CTC        816
His Ala Ser Lys Ile Leu Arg Phe Gln Lys Ile Thr Glu Asn Tyr Leu
            260                 265                 270

AAT GTT TTA TAT AAT TGC ACC GTG GCC AAC GAA GAA GCC ATA GAC ACC        864
Asn Val Leu Tyr Asn Cys Thr Val Ala Asn Glu Glu Ala Ile Asp Thr
        275                 280                 285

AAG AGC TTC GTC TTG GTG AGA AAA GAA ATA CCT GAT ATC CCA GGC CAT        912
Lys Ser Phe Val Leu Val Arg Lys Glu Ile Pro Asp Ile Pro Gly His
290                 295                 300

GTC TTT ACA                                                            921
Val Phe Thr
305

(2) INFORMATION FOR SEQ ID NO: 5:

(i) SEQUENCE CHARACTERISTICS:
        (A) LENGTH: 621 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY:mat peptide
        (B) LOCATION:1..621
        (C) IDENTIFICATION METHOD:S (xi) SEQUENCE DESCRIPTION: SEQ ID NO: 5:

GAA TCT TGT ACT TCA CGT CCC CAC ATT ACT GTG GTT GAA GGG GAA CCT         48
Glu Ser Cys Thr Ser Arg Pro His Ile Thr Val Val Glu Gly Glu Pro
  1               5                  10                  15

TTC TAT CTG AAA CAT TGC TCG TGT TCA CTT GCA CAT GAG ATT GAA ACA         96
```

```
Phe Tyr Leu Lys His Cys Ser Cys Ser Leu Ala His Glu Ile Glu Thr
            20                  25                  30

ACC ACC AAA AGC TGG TAC AAA AGC AGT GGA TCA CAG GAA CAT GTG GAG        144
Thr Thr Lys Ser Trp Tyr Lys Ser Ser Gly Ser Gln Glu His Val Glu
        35                  40                  45

CTG AAC CCA AGG AGT TCC TCG AGA ATT GCT TTG CAT GAT TGT GTT TTG        192
Leu Asn Pro Arg Ser Ser Ser Arg Ile Ala Leu His Asp Cys Val Leu
    50                  55                  60

GAG TTT TGG CCA GTT GAG TTG AAT GAC ACA GGA TCT TAC TTT TTC CAA        240
Glu Phe Trp Pro Val Glu Leu Asn Asp Thr Gly Ser Tyr Phe Phe Gln
65                  70                  75                  80

ATG AAA AAT TAT ACT CAG AAA TGG AAA TTA AAT GTC ATC AGA AGA AAT        288
Met Lys Asn Tyr Thr Gln Lys Trp Lys Leu Asn Val Ile Arg Arg Asn
            85                  90                  95

AAA CAC AGC TGT TTC ACT GAA AGA CAA GTA ACT AGT AAA ATT GTG GAA        336
Lys His Ser Cys Phe Thr Glu Arg Gln Val Thr Ser Lys Ile Val Glu
            100                 105                 110

GTT AAA AAA TTT TTT CAG ATA ACC TGT GAA AAC AGT TAC TAT CAA ACA        384
Val Lys Lys Phe Phe Gln Ile Thr Cys Glu Asn Ser Tyr Tyr Gln Thr
            115                 120                 125

CTG GTC AAC AGC ACA TCA TTG TAT AAG AAC TGT AAA AAG CTA CTA CTG        432
Leu Val Asn Ser Thr Ser Leu Tyr Lys Asn Cys Lys Lys Leu Leu Leu
    130                 135                 140

GAG AAC AAT AAA AAC CCA ACG ATA AAG AAG AAC GCC GAG TTT GAA GAT        480
Glu Asn Asn Lys Asn Pro Thr Ile Lys Lys Asn Ala Glu Phe Glu Asp
145                 150                 155                 160

GAG GGG TAT TAC TCC TGC GTG CAT TTC CTT CAT CAT AAT GGA AAA CTA        528
Gln Gly Tyr Tyr Ser Cys Val His Phe Leu His His Asn Gly Lys Leu
                165                 170                 175

TTT AAT ATC ACC AAA ACC TTC AAT ATA ACA ATA GTG GAA GAT CGC AGT        576
Phe Asn Ile Thr Lys Thr Phe Asn Ile Thr Ile Val Glu Asp Arg Ser
            180                 185                 190

AAT ATA GTT CCG GTT CTT CTT GGA CCA AAG CTT AAC CAT GTT GCA            621
Asn Ile Val Pro Val Leu Leu Gly Pro Lys Leu Asn His Val Ala
            195                 200                 205

(2) INFORMATION FOR SEQ ID NO: 6:

(i) SEQUENCE CHARACTERISTICS:
        (A) LENGTH: 927 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY:mat peptide
        (B) LOCATION:1..927
        (C) IDENTIFICATION METHOD:E (xi) SEQUENCE DESCRIPTION: SEQ ID NO: 6:

GAA TCT TGT ACT TCA CGT CCC CAC ATT ACT GTG GTT GAA GGG GAA CCT         48
Glu Ser Cys Thr Ser Arg Pro His Ile Thr Val Val Glu Gly Glu Pro
1               5                   10                  15

TTC TAT CTG AAA CAT TGC TCG TGT TCA CTT GCA CAT GAG ATT GAA ACA         96
Phe Tyr Leu Lys His Cys Ser Cys Ser Leu Ala His Glu Ile Glu Thr
            20                  25                  30

ACC ACC AAA AGC TGG TAC AAA AGC AGT GGA TCA CAG GAA CAT GTG GAG        144
Thr Thr Lys Ser Trp Tyr Lys Ser Ser Gly Ser Gln Glu His Val Glu
        35                  40                  45

CTG AAC CCA AGG AGT TCC TCG AGA ATT GCT TTG CAT GAT TGT GTT TTG        192
Leu Asn Pro Arg Ser Ser Ser Arg Ile Ala Leu His Asp Cys Val Leu
```

```
            50                      55                       60
GAG TTT TGG CCA GTT GAG TTG AAT GAC ACA GGA TCT TAC TTT TTC CAA     240
Glu Phe Trp Pro Val Glu Leu Asn Asp Thr Gly Ser Tyr Phe Phe Gln
 65                  70                      75                  80

ATG AAA AAT TAT ACT CAG AAA TGG AAA TTA AAT GTC ATC AGA AGA AAT     288
Met Lys Asn Tyr Thr Gln Lys Trp Lys Leu Asn Val Ile Arg Arg Asn
                 85                      90                  95

AAA CAC AGC TGT TTC ACT GAA AGA CAA GTA ACT AGT AAA ATT GTG GAA     336
Lys His Ser Cys Phe Thr Glu Arg Gln Val Thr Ser Lys Ile Val Glu
                    100                 105                 110

GTT AAA AAA TTT TTT CAG ATA ACC TGT GAA AAC AGT TAC TAT CAA ACA     384
Val Lys Lys Phe Phe Gln Ile Thr Cys Glu Asn Ser Tyr Tyr Gln Thr
             115                 120                 125

CTG GTC AAC AGC ACA TCA TTG TAT AAG AAC TGT AAA AAG CTA CTA CTG     432
Leu Val Asn Ser Thr Ser Leu Tyr Lys Asn Cys Lys Lys Leu Leu Leu
         130                 135                 140

GAG AAC AAT AAA AAC CCA ACG ATA AAG AAG AAC GCC GAG TTT GAA GAT     480
Glu Asn Asn Lys Asn Pro Thr Ile Lys Lys Asn Ala Glu Phe Glu Asp
145                 150                 155                 160

CAG GGG TAT TAC TCC TGC GTG CAT TTC CTT CAT CAT AAT GGA AAA CTA     528
Gln Gly Tyr Tyr Ser Cys Val His Phe Leu His His Asn Gly Lys Leu
                 165                 170                 175

TTT AAT ATC ACC AAA ACC TTC AAT ATA ACA ATA GTG GAA GAT CGC AGT     576
Phe Asn Ile Thr Lys Thr Phe Asn Ile Thr Ile Val Glu Asp Arg Ser
             180                 185                 190

AAT ATA GTT CCG GTT CTT CTT GGA CCA AAG CTT AAC CAT GTT GCA GTG     624
Asn Ile Val Pro Val Leu Leu Gly Pro Lys Leu Asn His Val Ala Val
         195                 200                 205

GAA TTA GGA AAA AAC GTA AGG CTC AAC TGC TCT GCT TTG CTG AAT GAA     672
Glu Leu Gly Lys Asn Val Arg Leu Asn Cys Ser Ala Leu Leu Asn Glu
210                 215                 220

GAG GAT GTA ATT TAT TGG ATG TTC GGG GAA GAA AAT GGA TCG GAT CCT     720
Glu Asp Val Ile Tyr Trp Met Phe Gly Glu Glu Asn Gly Ser Asp Pro
225                 230                 235                 240

AAT ATA CAT GAA GAG AAA GAA ATG AGA ATT ATG ACT CCA GAA GGC AAA     768
Asn Ile His Glu Glu Lys Glu Met Arg Ile Met Thr Pro Glu Gly Lys
                 245                 250                 255

TGG CAT GCT TCA AAA GTA TTG AGA ATT GAA AAT ATT GGT GAA AGC AAT     816
Trp His Ala Ser Lys Val Leu Arg Ile Glu Asn Ile Gly Glu Ser Asn
             260                 265                 270

CTA AAT GTT TTA TAT AAT TGC ACT GTG GCC AGC ACG GGA GGC ACA GAC     864
Leu Asn Val Leu Tyr Asn Cys Thr Val Ala Ser Thr Gly Gly Thr Asp
         275                 280                 285

ACC AAA AGC TTC ATC TTG GTG AGA AAA GAC ATG GCT GAT ATC CCA GGC     912
Thr Lys Ser Phe Ile Leu Val Arg Lys Asp Met Ala Asp Ile Pro Gly
290                 295                 300

CAC GTC TTC ACA AGA                                                 927
His Val Phe Thr Arg
305
```

(2) INFORMATION FOR SEQ ID NO: 7:

(i) SEQUENCE CHARACTERISTICS:
        (A) LENGTH: 1620 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: lymphoblastoid cell derived from a patient with Hodgkin's disease
    (C) INDIVIDUAL ISOLATE: L428 (FERM BP-5777)

(ix) FEATURE:
    (A) NAME/KEY:sig peptide
    (B) LOCATION:1..57
    (C) IDENTIFICATION METHOD:E (ix) FEATURE:
    (A) NAME/KEY:mat peptide
    (B) LOCATION:58..1620
    (C) IDENTIFICATION METHOD:E (xi) SEQUENCE DESCRIPTION: SEQ ID NO: 7:

```
ATG AAT TGT AGA GAA TTA CCC TTG ACC CTT TGG GTG CTT ATA TCT GTA        48
Met Asn Cys Arg Glu Leu Pro Leu Thr Leu Trp Val Leu Ile Ser Val
            -15                 -10                 -5

AGC ACT GCA GAA TCT TGT ACT TCA CGT CCC CAC ATT ACT GTG GTT GAA        96
Ser Thr Ala Glu Ser Cys Thr Ser Arg Pro His Ile Thr Val Val Glu
                1                   5                  10

GGG GAA CCT TTC TAT CTG AAA CAT TGC TCG TGT TCA CTT GCA CAT GAG       144
Gly Glu Pro Phe Tyr Leu Lys His Cys Ser Cys Ser Leu Ala His Glu
             15                  20                  25

ATT GAA ACA ACC ACC AAA AGC TGG TAC AAA AGC AGT GGA TCA CAG GAA       192
Ile Glu Thr Thr Thr Lys Ser Trp Tyr Lys Ser Ser Gly Ser Gln Glu
 30                  35                  40                  45

CAT GTG GAG CTG AAC CCA AGG AGT TCC TCG AGA ATT GCT TTG CAT GAT       240
His Val Glu Leu Asn Pro Arg Ser Ser Ser Arg Ile Ala Leu His Asp
                 50                  55                  60

TGT GTT TTG GAG TTT TGG CCA GTT GAG TTG AAT GAC ACA GGA TCT TAC       288
Cys Val Leu Glu Phe Trp Pro Val Glu Leu Asn Asp Thr Gly Ser Tyr
             65                  70                  75

TTT TTC CAA ATG AAA AAT TAT ACT CAG AAA TGG AAA TTA AAT GTC ATC       336
Phe Phe Gln Met Lys Asn Tyr Thr Gln Lys Trp Lys Leu Asn Val Ile
         80                  85                  90

AGA AGA AAT AAA CAC AGC TGT TTC ACT GAA AGA CAA GTA ACT AGT AAA       384
Arg Arg Asn Lys His Ser Cys Phe Thr Glu Arg Gln Val Thr Ser Lys
     95                 100                 105

ATT GTG GAA GTT AAA AAA TTT TTT CAG ATA ACC TGT GAA AAC AGT TAC       432
Ile Val Glu Val Lys Lys Phe Phe Gln Ile Thr Cys Glu Asn Ser Tyr
110                 115                 120                 125

TAT CAA ACA CTG GTC AAC AGC ACA TCA TTG TAT AAG AAC TGT AAA AAG       480
Tyr Gln Thr Leu Val Asn Ser Thr Ser Leu Tyr Lys Asn Cys Lys Lys
                130                 135                 140

CTA CTA CTG GAG AAC AAT AAA AAC CCA ACG ATA AAG AAG AAC GCC GAG       528
Leu Leu Leu Glu Asn Asn Lys Asn Pro Thr Ile Lys Lys Asn Ala Glu
            145                 150                 155

TTT GAA GAT CAG GGG TAT TAC TCC TGC GTG CAT TTC CTT CAT CAT AAT       576
Phe Glu Asp Gln Gly Tyr Tyr Ser Cys Val His Phe Leu His His Asn
        160                 165                 170

GGA AAA CTA TTT AAT ATC ACC AAA ACC TTC AAT ATA ACA ATA GTG GAA       624
Gly Lys Leu Phe Asn Ile Thr Lys Thr Phe Asn Ile Thr Ile Val Glu
    175                 180                 185

GAT CGC AGT AAT ATA GTT CCG GTT CTT CTT GGA CCA AAG CTT AAC CAT       672
Asp Arg Ser Asn Ile Val Pro Val Leu Leu Gly Pro Lys Leu Asn His
190                 195                 200                 205

GTT GCA GTG GAA TTA GGA AAA AAC GTA AGG CTC AAC TGC TCT GCT TTG       720
Val Ala Val Glu Leu Gly Lys Asn Val Arg Leu Asn Cys Ser Ala Leu
                210                 215                 220

CTG AAT GAA GAG GAT GTA ATT TAT TGG ATG TTC GGG GAA GAA AAT GGA       768
Leu Asn Glu Glu Asp Val Ile Tyr Trp Met Phe Gly Glu Glu Asn Gly
            225                 230                 235
```

-continued

```
TCG GAT CCT AAT ATA CAT GAA GAG AAA GAA ATG AGA ATT ATG ACT CCA      816
Ser Asp Pro Asn Ile His Glu Glu Lys Glu Met Arg Ile Met Thr Pro
        240                 245                 250

GAA GGC AAA TGG CAT GCT TCA AAA GTA TTG AGA ATT GAA AAT ATT GGT      864
Glu Gly Lys Trp His Ala Ser Lys Val Leu Arg Ile Glu Asn Ile Gly
255                 260                 265

GAA AGC AAT CTA AAT GTT TTA TAT AAT TGC ACT GTG GCC AGC ACG GGA      912
Glu Ser Asn Leu Asn Val Leu Tyr Asn Cys Thr Val Ala Ser Thr Gly
270                 275                 280                 285

GGC ACA GAC ACC AAA AGC TTC ATC TTG GTG AGA AAA GAC ATG GCT GAT      960
Gly Thr Asp Thr Lys Ser Phe Ile Leu Val Arg Lys Asp Met Ala Asp
                290                 295                 300

ATC CCA GGC CAC GTC TTC ACA AGA GGA ATG ATC ATA GCT GTT TTG ATC     1008
Ile Pro Gly His Val Phe Thr Arg Gly Met Ile Ile Ala Val Leu Ile
            305                 310                 315

TTG GTG GCA GTA GTG TGC CTA GTG ACT GTG TGT GTC ATT TAT AGA GTT     1056
Leu Val Ala Val Val Cys Leu Val Thr Val Cys Val Ile Tyr Arg Val
        320                 325                 330

GAC TTG GTT CTA TTT TAT AGA CAT TTA ACG AGA AGA GAT GAA ACA TTA     1104
Asp Leu Val Leu Phe Tyr Arg His Leu Thr Arg Arg Asp Glu Thr Leu
    335                 340                 345

ACA GAT GGA AAA ACA TAT GAT GCT TTT GTG TCT TAC CTA AAA GAA TGC     1152
Thr Asp Gly Lys Thr Tyr Asp Ala Phe Val Ser Tyr Leu Lys Glu Cys
350                 355                 360                 365

CGA CCT GAA AAT GGA GAG GAG CAC ACC TTT GCT GTG GAG ATT TTG CCC     1200
Arg Pro Glu Asn Gly Glu Glu His Thr Phe Ala Val Glu Ile Leu Pro
                370                 375                 380

AGG GTG TTG GAG AAA CAT TTT GGG TAT AAG TTA TGC ATA TTT GAA AGG     1248
Arg Val Leu Glu Lys His Phe Gly Tyr Lys Leu Cys Ile Phe Glu Arg
            385                 390                 395

GAT GTA GTG CCT GGA GGA GCT GTT GTT GAT GAA ATC CAC TCA CTG ATA     1296
Asp Val Val Pro Gly Gly Ala Val Val Asp Glu Ile His Ser Leu Ile
        400                 405                 410

GAG AAA AGC CGA AGA CTA ATC ATT GTC CTA AGT AAA AGT TAT ATG TCT     1344
Glu Lys Ser Arg Arg Leu Ile Ile Val Leu Ser Lys Ser Tyr Met Ser
    415                 420                 425

AAT GAG GTC AGG TAT GAA CTT GAA AGT GGA CTC CAT GAA GCA TTG GTG     1392
Asn Glu Val Arg Tyr Glu Leu Glu Ser Gly Leu His Glu Ala Leu Val
430                 435                 440                 445

GAA AGA AAA ATT AAA ATA ATC TTA ATT GAA TTT ACA CCT GTT ACT GAC     1440
Glu Arg Lys Ile Lys Ile Ile Leu Ile Glu Phe Thr Pro Val Thr Asp
                450                 455                 460

TTC ACA TTC TTG CCC CAA TCA CTA AAG CTT TTG AAA TCT CAC AGA GTT     1488
Phe Thr Phe Leu Pro Gln Ser Leu Lys Leu Leu Lys Ser His Arg Val
            465                 470                 475

CTG AAG TGG AAG GCC GAT AAA TCT CTT TCT TAT AAC TCA AGG TTC TGG     1536
Leu Lys Trp Lys Ala Asp Lys Ser Leu Ser Tyr Asn Ser Arg Phe Trp
        480                 485                 490

AAG AAC CTT CTT TAC TTA ATG CCT GCA AAA ACA GTC AAG CCA GGT AGA     1584
Lys Asn Leu Leu Tyr Leu Met Pro Ala Lys Thr Val Lys Pro Gly Arg
    495                 500                 505

GAC GAA CCG GAA GTC TTG CCT GTT CTT TCC GAG TCT                     1620
Asp Glu Pro Glu Val Leu Pro Val Leu Ser Glu Ser
510                 515                 520
```

(2) INFORMATION FOR SEQ ID NO: 8:

(i) SEQUENCE CHARACTERISTICS:
        (A) LENGTH: 369 base pairs
        (B) TYPE: nucleic acid
        (C) STRANDEDNESS: double (D) TOPOLOGY: linear (ii) MOLECULE TYPE: cDNA (ix) FEATURE:
   (A) NAME/KEY:sig peptide
   (B) LOCATION:1..57
   (C) IDENTIFICATION METHOD:S (ix) FEATURE:
   (A) NAME/KEY:mat peptide
   (B) LOCATION:58..369
   (C) IDENTIFICATION METHOD:S (xi) SEQUENCE DESCRIPTION: SEQ ID NO: 8:

```
ATG AAT TGT AGA GAA TTA CCC TTG ACC CTT TGG GTG CTT ATA TCT GTA       48
Met Asn Cys Arg Glu Leu Pro Leu Thr Leu Trp Val Leu Ile Ser Val
            -15             -10                 -5

AGC ACT GCA GAA TCT TGT ACT TCA CGT CCC CAC ATT ACT GTG GTT GAA       96
Ser Thr Ala Glu Ser Cys Thr Ser Arg Pro His Ile Thr Val Val Glu
             1               5                  10

GGG GAA CCT TTC TAT CTG AAA CAT TGC TCG TGT TCA CTT GCA CAT GAG      144
Gly Glu Pro Phe Tyr Leu Lys His Cys Ser Cys Ser Leu Ala His Glu
         15              20              25

ATT GAA ACA ACC ACC AAA AGC TGG TAC AAA AGC AGT GGA TCA CAG GAA      192
Ile Glu Thr Thr Thr Lys Ser Trp Tyr Lys Ser Ser Gly Ser Gln Glu
 30              35              40              45

CAT GTG GAG CTG AAC CCA AGG AGT TCC TCG AGA ATT GCT TTG CAT GAT      240
His Val Glu Leu Asn Pro Arg Ser Ser Ser Arg Ile Ala Leu His Asp
                 50              55              60

TGT GTT TTG GAG TTT TGG CCA GTT GAG TTG AAT GAC ACA GGA TCT TAC      288
Cys Val Leu Glu Phe Trp Pro Val Glu Leu Asn Asp Thr Gly Ser Tyr
             65              70              75

TTT TTC CAA ATG AAA AAT TAT ACT CAG AAA TGG AAA TTA AAT GTC ATC      336
Phe Phe Gln Met Lys Asn Tyr Thr Gln Lys Trp Lys Leu Asn Val Ile
         80              85              90

AGA AGA AAT AAA CAC AGC TGT TTC ACT GAA AGA                          369
Arg Arg Asn Lys His Ser Cys Phe Thr Glu Arg
 95              100
```

(2) INFORMATION FOR SEQ ID NO: 9:

(i) SEQUENCE CHARACTERISTICS:
    (A) LENGTH: 678 base pairs
    (B) TYPE: nucleic acid
    (C) STRANDEDNESS: double
    (D) TOPOLOGY: linear (ii) MOLECULE TYPE: cDNA (ix) FEATURE:
    (A) NAME/KEY:sig peptide
    (B) LOCATION:1..57
    (C) IDENTIFICATION METHOD:S (ix) FEATURE:
    (A) NAME/KEY:mat peptide
    (B) LOCATION:58..678
    (C) IDENTIFICATION METHOD:S (xi) SEQUENCE DESCRIPTION: SEQ ID NO: 9:

```
ATG AAT TGT AGA GAA TTA CCC TTG ACC CTT TGG GTG CTT ATA TCT GTA       48
Met Asn Cys Arg Glu Leu Pro Leu Thr Leu Trp Val Leu Ile Ser Val
            -15             -10                 -5

AGC ACT GCA GAA TCT TGT ACT TCA CGT CCC CAC ATT ACT GTG GTT GAA       96
Ser Thr Ala Glu Ser Cys Thr Ser Arg Pro His Ile Thr Val Val Glu
             1               5                  10
```

```
GGG GAA CCT TTC TAT CTG AAA CAT TGC TCG TGT TCA CTT GCA CAT GAG      144
Gly Glu Pro Phe Tyr Leu Lys His Cys Ser Cys Ser Leu Ala His Glu
         15                  20                  25

ATT GAA ACA ACC ACC AAA AGC TGG TAC AAA AGC AGT GGA TCA CAG GAA      192
Ile Glu Thr Thr Thr Lys Ser Trp Tyr Lys Ser Ser Gly Ser Gln Glu
 30                  35                  40                  45

CAT GTG GAG CTG AAC CCA AGG AGT TCC TCG AGA ATT GCT TTG CAT GAT      240
His Val Glu Leu Asn Pro Arg Ser Ser Ser Arg Ile Ala Leu His Asp
                 50                  55                  60

TGT GTT TTG GAG TTT TGG CCA GTT GAG TTG AAT GAC ACA GGA TCT TAC      288
Cys Val Leu Glu Phe Trp Pro Val Glu Leu Asn Asp Thr Gly Ser Tyr
             65                  70                  75

TTT TTC CAA ATG AAA AAT TAT ACT CAG AAA TGG AAA TTA AAT GTC ATC      336
Phe Phe Gln Met Lys Asn Tyr Thr Gln Lys Trp Lys Leu Asn Val Ile
         80                  85                  90

AGA AGA AAT AAA CAC AGC TGT TTC ACT GAA AGA CAA GTA ACT AGT AAA      384
Arg Arg Asn Lys His Ser Cys Phe Thr Glu Arg Gln Val Thr Ser Lys
     95                 100                 105

ATT GTG GAA GTT AAA AAA TTT TTT CAG ATA ACC TGT GAA AAC AGT TAC      432
Ile Val Glu Val Lys Lys Phe Phe Gln Ile Thr Cys Glu Asn Ser Tyr
110                 115                 120                 125

TAT CAA ACA CTG GTC AAC AGC ACA TCA TTG TAT AAG AAC TGT AAA AAG      480
Tyr Gln Thr Leu Val Asn Ser Thr Ser Leu Tyr Lys Asn Cys Lys Lys
                130                 135                 140

CTA CTA CTG GAG AAC AAT AAA AAC CCA ACG ATA AAG AAG AAC GCC GAG      528
Leu Leu Leu Glu Asn Asn Lys Asn Pro Thr Ile Lys Lys Asn Ala Glu
            145                 150                 155

TTT GAA GAT CAG GGG TAT TAC TCC TGC GTG CAT TTC CTT CAT CAT AAT      576
Phe Glu Asp Gln Gly Tyr Tyr Ser Cys Val His Phe Leu His His Asn
        160                 165                 170

GGA AAA CTA TTT AAT ATC ACC AAA ACC TTC AAT ATA ACA ATA GTG GAA      624
Gly Lys Leu Phe Asn Ile Thr Lys Thr Phe Asn Ile Thr Ile Val Glu
175                 180                 185

GAT CGC AGT AAT ATA GTT CCG GTT CTT CTT GGA CCA AAG CTT AAC CAT      672
Asp Arg Ser Asn Ile Val Pro Val Leu Leu Gly Pro Lys Leu Asn His
190                 195                 200                 205

GTT GCA                                                              678
Val Ala (2) INFORMATION FOR SEQ ID NO: 10:

(i) SEQUENCE CHARACTERISTICS:
        (A) LENGTH: 984 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY:sig peptide
        (B) LOCATION:1..57
        (C) IDENTIFICATION METHOD:E (ix) FEATURE:
        (A) NAME/KEY:mat peptide
        (B) LOCATION:58..984
        (C) IDENTIFICATION METHOD:E (xi) SEQUENCE DESCRIPTION: SEQ ID NO: 10:

ATG AAT TGT AGA GAA TTA CCC TTG ACC CTT TGG GTG CTT ATA TCT GTA       48
Met Asn Cys Arg Glu Leu Pro Leu Thr Leu Trp Val Leu Ile Ser Val
                -15                 -10                  -5

AGC ACT GCA GAA TCT TGT ACT TCA CGT CCC CAC ATT ACT GTG GTT GAA       96
```

```
Ser Thr Ala Glu Ser Cys Thr Ser Arg Pro His Ile Thr Val Val Glu
            1                   5                  10

GGG GAA CCT TTC TAT CTG AAA CAT TGC TCG TGT TCA CTT GCA CAT GAG        144
Gly Glu Pro Phe Tyr Leu Lys His Cys Ser Cys Ser Leu Ala His Glu
 15                  20                  25

ATT GAA ACA ACC ACC AAA AGC TGG TAC AAA AGC AGT GGA TCA CAG GAA        192
Ile Glu Thr Thr Thr Lys Ser Trp Tyr Lys Ser Ser Gly Ser Gln Glu
 30                  35                  40                  45

CAT GTG GAG CTG AAC CCA AGG AGT TCC TCG AGA ATT GCT TTG CAT GAT        240
His Val Glu Leu Asn Pro Arg Ser Ser Ser Arg Ile Ala Leu His Asp
             50                  55                  60

TGT GTT TTG GAG TTT TGG CCA GTT GAG TTG AAT GAC ACA GGA TCT TAC        288
Cys Val Leu Glu Phe Trp Pro Val Glu Leu Asn Asp Thr Gly Ser Tyr
             65                  70                  75

TTT TTC CAA ATG AAA AAT TAT ACT CAG AAA TGG AAA TTA AAT GTC ATC        336
Phe Phe Gln Met Lys Asn Tyr Thr Gln Lys Trp Lys Leu Asn Val Ile
         80                  85                  90

AGA AGA AAT AAA CAC AGC TGT TTC ACT GAA AGA CAA GTA ACT AGT AAA        384
Arg Arg Asn Lys His Ser Cys Phe Thr Glu Arg Gln Val Thr Ser Lys
 95                 100                 105

ATT GTG GAA GTT AAA AAA TTT TTT CAG ATA ACC TGT GAA AAC AGT TAC        432
Ile Val Glu Val Lys Lys Phe Phe Gln Ile Thr Cys Glu Asn Ser Tyr
110                 115                 120                 125

TAT CAA ACA CTG GTC AAC AGC ACA TCA TTG TAT AAG AAC TGT AAA AAG        480
Tyr Gln Thr Leu Val Asn Ser Thr Ser Leu Tyr Lys Asn Cys Lys Lys
             130                 135                 140

CTA CTA CTG GAG AAC AAT AAA AAC CCA ACG ATA AAG AAG AAC GCC GAG        528
Leu Leu Leu Glu Asn Asn Lys Asn Pro Thr Ile Lys Lys Asn Ala Glu
             145                 150                 155

TTT GAA GAT CAG GGG TAT TAC TCC TGC GTG CAT TTC CTT CAT CAT AAT        576
Phe Glu Asp Gln Gly Tyr Tyr Ser Cys Val His Phe Leu His His Asn
             160                 165                 170

GGA AAA CTA TTT AAT ATC ACC AAA ACC TTC AAT ATA ACA ATA GTG GAA        624
Gly Lys Leu Phe Asn Ile Thr Lys Thr Phe Asn Ile Thr Ile Val Glu
175                 180                 185

GAT CGC AGT AAT ATA GTT CCG GTT CTT CTT GGA CCA AAG CTT AAC CAT        672
Asp Arg Ser Asn Ile Val Pro Val Leu Leu Gly Pro Lys Leu Asn His
190                 195                 200                 205

GTT GCA GTG GAA TTA GGA AAA AAC GTA AGG CTC AAC TGC TCT GCT TTG        720
Val Ala Val Glu Leu Gly Lys Asn Val Arg Leu Asn Cys Ser Ala Leu
             210                 215                 220

CTG AAT GAA GAG GAT GTA ATT TAT TGG ATG TTC GGG GAA GAA AAT GGA        768
Leu Asn Glu Glu Asp Val Ile Tyr Trp Met Phe Gly Glu Glu Asn Gly
             225                 230                 235

TCG GAT CCT AAT ATA CAT GAA GAG AAA GAA ATG AGA ATT ATG ACT CCA        816
Ser Asp Pro Asn Ile His Glu Glu Lys Glu Met Arg Ile Met Thr Pro
             240                 245                 250

GAA GGC AAA TGG CAT GCT TCA AAA GTA TTG AGA ATT GAA AAT ATT GGT        864
Glu Gly Lys Trp His Ala Ser Lys Val Leu Arg Ile Glu Asn Ile Gly
255                 260                 265

GAA AGC AAT CTA AAT GTT TTA TAT AAT TGC ACT GTG GCC AGC ACG GGA        912
Glu Ser Asn Leu Asn Val Leu Tyr Asn Cys Thr Val Ala Ser Thr Gly
270                 275                 280                 285

GGC ACA GAC ACC AAA AGC TTC ATC TTG GTG AGA AAA GAC ATG GCT GAT        960
Gly Thr Asp Thr Lys Ser Phe Ile Leu Val Arg Lys Asp Met Ala Asp
             290                 295                 300

ATC CCA GGC CAC GTC TTC ACA AGA                                        984
Ile Pro Gly His Val Phe Thr Arg
             305
```

(2) INFORMATION FOR SEQ ID NO: 11:

(i) SEQUENCE CHARACTERISTICS:
        (A) LENGTH: 975 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY:sig peptide
        (B) LOCATION:1..54
        (C) IDENTIFICATION METHOD:S (ix) FEATURE:
        (A) NAME/KEY:mat peptide
        (B) LOCATION:55..975
        (C) IDENTIFICATION METHOD:S (xi) SEQUENCE DESCRIPTION: SEQ ID NO: 11:

```
ATG CAT CAT GAA GAA TTA ATC TTG ACA CTC TGC ATT CTC ATT GTT AAA      48
Met His His Glu Glu Leu Ile Leu Thr Leu Cys Ile Leu Ile Val Lys
            -15                 -10                 -5

AGT GCC TCA AAA AGT TGT ATT CAC CGA TCA CAA ATT CAT GTG GTA GAG      96
Ser Ala Ser Lys Ser Cys Ile His Arg Ser Gln Ile His Val Val Glu
          1               5                  10

GGA GAA CCT TTT TAT CTG AAG CCA TGT GGC ATA TCT GCA CCA GTG CAC     144
Gly Glu Pro Phe Tyr Leu Lys Pro Cys Gly Ile Ser Ala Pro Val His
 15                  20                  25                  30

AGG AAT GAA ACA GCC ACC ATG AGA TGG TTC AAA GGC AGT GCT TCA CAT     192
Arg Asn Glu Thr Ala Thr Met Arg Trp Phe Lys Gly Ser Ala Ser His
                 35                  40                  45

GAG TAT AGA GAG CTG AAC AAC AGA AGC TCG CCC AGA GTC ACT TTT CAT     240
Glu Tyr Arg Glu Leu Asn Asn Arg Ser Ser Pro Arg Val Thr Phe His
             50                  55                  60

GAT CAC ACC TTG GAA TTC TGG CCA GTT GAG ATG GAG GAT GAG GGA ACG     288
Asp His Thr Leu Glu Phe Trp Pro Val Glu Met Glu Asp Glu Gly Thr
             65                  70                  75

TAC ATT TCT CAA GTC GGA AAT GAT CGT CGC AAT TGG ACC TTA AAT GTC     336
Tyr Ile Ser Gln Val Gly Asn Asp Arg Arg Asn Trp Thr Leu Asn Val
         80                  85                  90

ACC AAA AGA AAC AAA CAC AGC TGT TTC TCT GAC AAG CTC GTG ACA AGC     384
Thr Lys Arg Asn Lys His Ser Cys Phe Ser Asp Lys Leu Val Thr Ser
 95                 100                 105                 110

AGA GAT GTT GAA GTT AAC AAA TCT CTG CAT ATC ACT TGT AAG AAT CCT     432
Arg Asp Val Glu Val Asn Lys Ser Leu His Ile Thr Cys Lys Asn Pro
                 115                 120                 125

AAC TAT GAA GAG CTG ATC CAG GAC ACA TGG CTG TAT AAG AAC TGT AAG     480
Asn Tyr Glu Glu Leu Ile Gln Asp Thr Trp Leu Tyr Lys Asn Cys Lys
             130                 135                 140

GAA ATA TCC AAA ACC CCA AGG ATC CTG AAG GAT GCC GAG TTT GGA GAT     528
Glu Ile Ser Lys Thr Pro Arg Ile Leu Lys Asp Ala Glu Phe Gly Asp
             145                 150                 155

GAG GGC TAC TAC TCC TGC GTG TTT TCT GTC CAC CAT AAT GGG ACA CGG     576
Glu Gly Tyr Tyr Ser Cys Val Phe Ser Val His His Asn Gly Thr Arg
 160                 165                 170

TAC AAC ATC ACC AAG ACT GTC AAT ATA ACA GTT ATT GAA GGA AGG AGT     624
Tyr Asn Ile Thr Lys Thr Val Asn Ile Thr Val Ile Glu Gly Arg Ser
175                 180                 185                 190

AAA GTA ACT CCA GCT ATT TTA GGA CCA AAG TGT GAG AAG GTT GGT GTA     672
Lys Val Thr Pro Ala Ile Leu Gly Pro Lys Cys Glu Lys Val Gly Val
                 195                 200                 205
```

```
GAA CTA GGA AAG GAT GTG GAG TTG AAC TGC AGT GCT TCA TTG AAT AAA      720
Glu Leu Gly Lys Asp Val Glu Leu Asn Cys Ser Ala Ser Leu Asn Lys
            210                 215                 220

GAC GAT CTG TTT TAT TGG AGC ATC AGG AAA GAG GAC AGC TCA GAC CCT      768
Asp Asp Leu Phe Tyr Trp Ser Ile Arg Lys Glu Asp Ser Ser Asp Pro
                225                 230                 235

AAT GTG CAA GAA GAC AGG AAG GAG ACG ACA ACA TGG ATT TCT GAA GGC      816
Asn Val Gln Glu Asp Arg Lys Glu Thr Thr Thr Trp Ile Ser Glu Gly
        240                 245                 250

AAA CTG CAT GCT TCA AAA ATA CTG AGA TTT CAG AAA ATT ACT GAA AAC      864
Lys Leu His Ala Ser Lys Ile Leu Arg Phe Gln Lys Ile Thr Glu Asn
255                 260                 265                 270

TAT CTC AAT GTT TTA TAT AAT TGC ACC GTG GCC AAC GAA GAA GCC ATA      912
Tyr Leu Asn Val Leu Tyr Asn Cys Thr Val Ala Asn Glu Glu Ala Ile
                275                 280                 285

GAC ACC AAG AGC TTC GTC TTG GTG AGA AAA GAA ATA CCT GAT ATC CCA      960
Asp Thr Lys Ser Phe Val Leu Val Arg Lys Glu Ile Pro Asp Ile Pro
            290                 295                 300

GGC CAT GTC TTT ACA                                                  975
Gly His Val Phe Thr
        305

(2) INFORMATION FOR SEQ ID NO: 12:

(i) SEQUENCE CHARACTERISTICS:
        (A) LENGTH: 5
        (B) TYPE: amino acid
        (D) TOPOLOGY: linear (ii) MOLECULE TYPE: peptide (v) FRAGMENT TYPE: internal fragment (xi) SEQUENCE DESCRIPTION: SEQ ID NO: 12:

Trp His Ala Ser Lys
 1

(2) INFORMATION FOR SEQ ID NO: 13:

(i) SEQUENCE CHARACTERISTICS:
        (A) LENGTH: 7
        (B) TYPE: amino acid
        (D) TOPOLOGY: linear (ii) MOLECULE TYPE: peptide (v) FRAGMENT TYPE: internal fragment (xi) SEQUENCE DESCRIPTION: SEQ ID NO: 13:

Ile Met Thr Pro Glu Gly Lys
 1               5

(2) INFORMATION FOR SEQ ID NO: 14:

(i) SEQUENCE CHARACTERISTICS:
        (A) LENGTH: 13
        (B) TYPE: amino acid
        (D) TOPOLOGY: linear (ii) MOLECULE TYPE: peptide (v) FRAGMENT TYPE: internal fragment (xi) SEQUENCE DESCRIPTION: SEQ ID NO: 14:

Ser Ser Gly Ser Gln Glu His Val Glu Leu Asn Pro Arg
 1               5                  10
```

(2) INFORMATION FOR SEQ ID NO: 15:

(i) SEQUENCE CHARACTERISTICS:
        (A) LENGTH: 4
        (B) TYPE: amino acid
        (D) TOPOLOGY: linear (ii) MOLECULE TYPE: peptide (v) FRAGMENT TYPE: internal fragment (xi) SEQUENCE DESCRIPTION: SEQ ID NO: 15:

```
Ser Trp Tyr Lys
 1
```

(2) INFORMATION FOR SEQ ID NO: 16:

(i) SEQUENCE CHARACTERISTICS:
        (A) LENGTH: 10
        (B) TYPE: amino acid
        (D) TOPOLOGY: linear (ii) MOLECULE TYPE: peptide (v) FRAGMENT TYPE: internal fragment (xi) SEQUENCE DESCRIPTION: SEQ ID NO: 16:

```
Leu Asn His Val Ala Val Glu Leu Gly Lys
 1               5                  10
```

(2) INFORMATION FOR SEQ ID NO: 17:

(i) SEQUENCE CHARACTERISTICS:
        (A) LENGTH: 6
        (B) TYPE: amino acid
        (D) TOPOLOGY: linear (ii) MOLECULE TYPE: peptide (v) FRAGMENT TYPE: internal fragment (xi) SEQUENCE DESCRIPTION: SEQ ID NO: 17:

```
Ser Phe Ile Leu Val Arg
 1               5
```

(2) INFORMATION FOR SEQ ID NO: 18:

(i) SEQUENCE CHARACTERISTICS:
        (A) LENGTH: 15
        (B) TYPE: amino acid
        (D) TOPOLOGY: linear (ii) MOLECULE TYPE: peptide (v) FRAGMENT TYPE: internal fragment (xi) SEQUENCE DESCRIPTION: SEQ ID NO: 18:

```
Thr Val Lys Pro Gly Arg Asp Glu Pro Glu Val Leu Pro Val Leu
 1               5                  10                  15
```

(2) INFORMATION FOR SEQ ID NO: 19:

(i) SEQUENCE CHARACTERISTICS:
        (A) LENGTH: 11
        (B) TYPE: amino acid
        (D) TOPOLOGY: linear (ii) MOLECULE TYPE: peptide (v) FRAGMENT TYPE: internal fragment (xi) SEQUENCE DESCRIPTION: SEQ ID NO: 19:

Ser Asn Ile Val Pro Val Leu Leu Gly Pro Lys
 1               5                  10

(2) INFORMATION FOR SEQ ID NO: 20:

(i) SEQUENCE CHARACTERISTICS:
        (A) LENGTH: 521
        (B) TYPE: amino acid
        (D) TOPOLOGY: linear (ii) MOLECULE TYPE: peptide (xi) SEQUENCE DESCRIPTION: SEQ ID NO: 20:

Glu Ser Cys Thr Ser Arg Pro His Ile Thr Val Val Glu Gly Glu Pro
 1               5                  10                  15

Phe Tyr Leu Lys His Cys Ser Cys Ser Leu Ala His Glu Ile Glu Thr
                20                  25                  30

Thr Thr Lys Ser Trp Tyr Lys Ser Gly Ser Gln Glu His Val Glu
         35                  40                  45

Leu Asn Pro Arg Ser Ser Arg Ile Ala Leu His Asp Cys Val Leu
     50                  55                  60

Glu Phe Trp Pro Val Glu Leu Asn Asp Thr Gly Ser Tyr Phe Phe Gln
 65                  70                  75                  80

Met Lys Asn Tyr Thr Gln Lys Trp Lys Leu Asn Val Ile Arg Arg Asn
                 85                  90                  95

Lys His Ser Cys Phe Thr Glu Arg Gln Val Thr Ser Lys Ile Val Glu
                100                 105                 110

Val Lys Lys Phe Phe Gln Ile Thr Cys Glu Asn Ser Tyr Tyr Gln Thr
                115                 120                 125

Leu Val Asn Ser Thr Ser Leu Tyr Lys Asn Cys Lys Lys Leu Leu Leu
            130                 135                 140

Glu Asn Asn Lys Asn Pro Thr Ile Lys Lys Asn Ala Glu Phe Glu Asp
145                 150                 155                 160

Gln Gly Tyr Tyr Ser Cys Val His Phe Leu His His Asn Gly Lys Leu
                165                 170                 175

Phe Asn Ile Thr Lys Thr Phe Asn Ile Thr Ile Val Glu Asp Arg Ser
                180                 185                 190

Asn Ile Val Pro Val Leu Leu Gly Pro Lys Leu Asn His Val Ala Val
            195                 200                 205

Glu Leu Gly Lys Asn Val Arg Leu Asn Cys Ser Ala Leu Leu Asn Glu
210                 215                 220

Glu Asp Val Ile Tyr Trp Met Phe Gly Glu Glu Asn Gly Ser Asp Pro
225                 230                 235                 240

Asn Ile His Glu Glu Lys Glu Met Arg Ile Met Thr Pro Glu Gly Lys
                245                 250                 255

Trp His Ala Ser Lys Val Leu Arg Ile Glu Asn Ile Gly Glu Ser Asn
                260                 265                 270

Leu Asn Val Leu Tyr Asn Cys Thr Val Ala Ser Thr Gly Gly Thr Asp
            275                 280                 285

Thr Lys Ser Phe Ile Leu Val Arg Lys Asp Met Ala Asp Ile Pro Gly
        290                 295                 300

His Val Phe Thr Arg Gly Met Ile Ile Ala Val Leu Ile Leu Val Ala
305                 310                 315                 320

Val Val Cys Leu Val Thr Val Cys Val Ile Tyr Arg Val Asp Leu Val

```
                    325                 330                 335
Leu Phe Tyr Arg His Leu Thr Arg Arg Asp Glu Thr Leu Thr Asp Gly
                340                 345                 350
Lys Thr Tyr Asp Ala Phe Val Ser Tyr Leu Lys Glu Cys Arg Pro Glu
                355                 360                 365
Asn Gly Glu Glu His Thr Phe Ala Val Glu Ile Leu Pro Arg Val Leu
            370                 375                 380
Glu Lys His Phe Gly Tyr Lys Leu Cys Ile Phe Glu Arg Asp Val Val
385                 390                 395                 400
Pro Gly Gly Ala Val Val Asp Glu Ile His Ser Leu Ile Glu Lys Ser
                405                 410                 415
Arg Arg Leu Ile Ile Val Leu Ser Lys Ser Tyr Met Ser Asn Glu Val
                420                 425                 430
Arg Tyr Glu Leu Glu Ser Gly Leu His Glu Ala Leu Val Glu Arg Lys
                435                 440                 445
Ile Lys Ile Ile Leu Ile Glu Phe Thr Pro Val Thr Asp Phe Thr Phe
            450                 455                 460
Leu Pro Gln Ser Leu Lys Leu Leu Lys Ser His Arg Val Leu Lys Trp
465                 470                 475                 480
Lys Ala Asp Lys Ser Leu Ser Tyr Asn Ser Arg Phe Trp Lys Asn Leu
                485                 490                 495
Leu Tyr Leu Met Pro Ala Lys Thr Val Lys Pro Gly Arg Asp Glu Pro
                500                 505                 510
Glu Val Leu Pro Val Leu Ser Glu Ser
                515                 520

(2) INFORMATION FOR SEQ ID NO: 21:

(i) SEQUENCE CHARACTERISTICS:
        (A) LENGTH: 519
        (B) TYPE: amino acid
        (D) TOPOLOGY: linear (ii) MOLECULE TYPE: peptide (xi) SEQUENCE DESCRIPTION: SEQ ID NO: 21:

Ser Lys Ser Cys Ile His Arg Ser Gln Ile His Val Val Glu Gly Glu
1               5                   10                  15
Pro Phe Tyr Leu Lys Pro Cys Gly Ile Ser Ala Pro Val His Arg Asn
                20                  25                  30
Glu Thr Ala Thr Met Arg Trp Phe Lys Gly Ser Ala Ser His Glu Tyr
            35                  40                  45
Arg Glu Leu Asn Asn Arg Ser Ser Pro Arg Val Thr Phe His Asp His
        50                  55                  60
Thr Leu Glu Phe Trp Pro Val Glu Met Glu Asp Glu Gly Thr Tyr Ile
65                  70                  75                  80
Ser Gln Val Gly Asn Asp Arg Arg Asn Trp Thr Leu Asn Val Thr Lys
                85                  90                  95
Arg Asn Lys His Ser Cys Phe Ser Asp Lys Leu Val Thr Ser Arg Asp
                100                 105                 110
Val Glu Val Asn Lys Ser Leu His Ile Thr Cys Lys Asn Pro Asn Tyr
            115                 120                 125
Glu Glu Leu Ile Gln Asp Thr Trp Leu Tyr Lys Asn Cys Lys Glu Ile
        130                 135                 140
Ser Lys Thr Pro Arg Ile Leu Lys Asp Ala Glu Phe Gly Asp Glu Gly
145                 150                 155                 160
```

-continued

```
Tyr Tyr Ser Cys Val Phe Ser Val His His Asn Gly Thr Arg Tyr Asn
                165                 170                 175
Ile Thr Lys Thr Val Asn Ile Thr Val Ile Glu Gly Arg Ser Lys Val
            180                 185                 190
Thr Pro Ala Ile Leu Gly Pro Lys Cys Glu Lys Val Gly Val Glu Leu
        195                 200                 205
Gly Lys Asp Val Glu Leu Asn Cys Ser Ala Ser Leu Asn Lys Asp Asp
    210                 215                 220
Leu Phe Tyr Trp Ser Ile Arg Lys Glu Asp Ser Ser Asp Pro Asn Val
225                 230                 235                 240
Gln Glu Asp Arg Lys Glu Thr Thr Thr Trp Ile Ser Glu Gly Lys Leu
                245                 250                 255
His Ala Ser Lys Ile Leu Arg Phe Gln Lys Ile Thr Glu Asn Tyr Leu
            260                 265                 270
Asn Val leu Tyr Asn Cys Thr Val Ala Asn Glu Ala Ile Asp Thr
        275                 280                 285
Lys Ser Phe Val Leu Val Arg Lys Glu Ile Pro Asp Ile Pro Gly His
    290                 295                 300
Val Phe Thr Gly Gly Val Thr Val Leu Val Leu Ala Ser Val Ala Ala
305                 310                 315                 320
Val Cys Ile Val Ile Leu Cys Val Ile Tyr Lys Val Asp Leu Val Leu
                325                 330                 335
Phe Tyr Arg Arg Ile Ala Glu Arg Asp Glu Thr Leu Thr Asp Gly Lys
            340                 345                 350
Thr Tyr Asp Ala Phe Val Ser Tyr Leu Lys Glu Cys His Pro Glu Asn
        355                 360                 365
Lys Glu Glu Tyr Thr Phe Ala Val Glu Thr Leu Pro Arg Val Leu Glu
    370                 375                 380
Lys Gln Phe Gly Tyr Lys Leu Cys Ile Phe Glu Arg Asp Val Val Pro
385                 390                 395                 400
Gly Gly Ala Val Val Glu Glu Ile His Ser Leu Ile Glu Lys Ser Arg
                405                 410                 415
Arg Leu Ile Ile Val Leu Ser Gln Ser Tyr Leu Thr Asn Gly Ala Arg
            420                 425                 430
Arg Glu Leu Glu Ser Gly Leu His Glu Ala Leu Val Glu Arg Lys Ile
        435                 440                 445
Lys Ile Ile Leu Ile Glu Phe Thr Pro Ala Ser Asn Ile Thr Phe Leu
    450                 455                 460
Pro Pro Ser Leu Lys Leu Leu Lys Ser Tyr Arg Val Leu Lys Trp Arg
465                 470                 475                 480
Ala Asp Ser Pro Ser Met Asn Ser Arg Phe Trp Lys Asn Leu Val Tyr
                485                 490                 495
Leu Met Pro Ala Lys Ala Val Lys Pro Trp Arg Glu Glu Ser Glu Ala
            500                 505                 510
Arg Ser Val Leu Ser Ala Pro
        515
```

(2) INFORMATION FOR SEQ ID NO: 22:

(i) SEQUENCE CHARACTERISTICS:
        (A) LENGTH: 309
        (B) TYPE: amino acid
        (D) TOPOLOGY: linear (ii) MOLECULE TYPE: peptide (xi) SEQUENCE DESCRIPTION: SEQ ID NO: 22:

Glu Ser Cys Thr Ser Arg Pro His Ile Thr Val Val Glu Gly Glu Pro
1               5                   10                  15

Phe Tyr Leu Lys His Cys Ser Cys Ser Leu Ala His Glu Ile Glu Thr
                20                  25                  30

Thr Thr Lys Ser Trp Tyr Lys Ser Gly Ser Gln Glu His Val Glu
            35                  40                  45

Leu Asn Pro Arg Ser Ser Arg Ile Ala Leu His Asp Cys Val Leu
50                  55                  60

Glu Phe Trp Pro Val Glu Leu Asn Asp Thr Gly Ser Tyr Phe Phe Gln
65                  70                  75                  80

Met Lys Asn Tyr Thr Gln Lys Trp Lys Leu Asn Val Ile Arg Arg Asn
                85                  90                  95

Lys His Ser Cys Phe Thr Glu Arg Gln Val Thr Ser Lys Ile Val Glu
                100                 105                 110

Val Lys Lys Phe Phe Gln Ile Thr Cys Glu Asn Ser Tyr Tyr Gln Thr
            115                 120                 125

Leu Val Asn Ser Thr Ser Leu Tyr Lys Asn Cys Lys Lys Leu Leu Leu
130                 135                 140

Glu Asn Asn Lys Asn Pro Thr Ile Lys Lys Asn Ala Glu Phe Glu Asp
145                 150                 155                 160

Gln Gly Tyr Tyr Ser Cys Val His Phe Leu His His Asn Gly Lys Leu
                165                 170                 175

Phe Asn Ile Thr Lys Thr Phe Asn Ile Thr Ile Val Glu Asp Arg Ser
            180                 185                 190

Asn Ile Val Pro Val Leu Leu Gly Pro Lys Leu Asn His Val Ala Val
            195                 200                 205

Glu Leu Gly Lys Asn Val Arg Leu Asn Cys Ser Ala Leu Leu Asn Glu
        210                 215                 220

Glu Asp Val Ile Tyr Trp Met Phe Gly Glu Glu Asn Gly Ser Asp Pro
225                 230                 235                 240

Asn Ile His Glu Glu Lys Glu Met Arg Ile Met Thr Pro Glu Gly Lys
                245                 250                 255

Trp His Ala Ser Lys Val Leu Arg Ile Glu Asn Ile Gly Glu Ser Asn
                260                 265                 270

Leu Asn Val Leu Tyr Asn Cys Thr Val Ala Ser Thr Gly Gly Thr Asp
            275                 280                 285

Thr Lys Ser Phe Ile Leu Val Arg Lys Asp Met Ala Asp Ile Pro Gly
290                 295                 300

His Val Phe Thr Arg
305

(2) INFORMATION FOR SEQ ID NO: 23:

(i) SEQUENCE CHARACTERISTICS:
        (A) LENGTH: 207
        (B) TYPE: amino acid
        (D) TOPOLOGY: linear (ii) MOLECULE TYPE: peptide (xi) SEQUENCE DESCRIPTION: SEQ ID NO: 23:

Glu Ser Cys Thr Ser Arg Pro His Ile Thr Val Val Glu Gly Glu Pro
1               5                   10                  15

Phe Tyr Leu Lys His Cys Ser Cys Ser Leu Ala His Glu Ile Glu Thr

```
                     20                  25                  30
Thr Thr Lys Ser Trp Tyr Lys Ser Ser Gly Ser Gln Glu His Val Glu
         35                  40                  45
Leu Asn Pro Arg Ser Ser Arg Ile Ala Leu His Asp Cys Val Leu
     50                  55                  60
Glu Phe Trp Pro Val Glu Leu Asn Asp Thr Gly Ser Tyr Phe Phe Gln
 65                  70                  75                  80
Met Lys Asn Tyr Thr Gln Lys Trp Lys Leu Asn Val Ile Arg Arg Asn
                 85                  90                  95
Lys His Ser Cys Phe Thr Glu Arg Gln Val Thr Ser Lys Ile Val Glu
                100                 105                 110
Val Lys Lys Phe Phe Gln Ile Thr Cys Glu Asn Ser Tyr Tyr Gln Thr
             115                 120                 125
Leu Val Asn Ser Thr Ser Leu Tyr Lys Asn Cys Lys Lys Leu Leu Leu
         130                 135                 140
Glu Asn Asn Lys Asn Pro Thr Ile Lys Lys Asn Ala Glu Phe Glu Asp
145                 150                 155                 160
Gln Gly Tyr Tyr Ser Cys Val His Phe Leu His His Asn Gly Lys Leu
                 165                 170                 175
Phe Asn Ile Thr Lys Thr Phe Asn Ile Thr Ile Val Glu Asp Arg Ser
             180                 185                 190
Asn Ile Val Pro Val Leu Leu Gly Pro Lys Leu Asn His Val Ala
         195                 200                 205

(2) INFORMATION FOR SEQ ID NO: 24:

(i) SEQUENCE CHARACTERISTICS:
        (A) LENGTH: 104
        (B) TYPE: amino acid
        (D) TOPOLOGY: linear (ii) MOLECULE TYPE: peptide (xi) SEQUENCE DESCRIPTION: SEQ ID NO: 24:

Glu Ser Cys Thr Ser Arg Pro His Ile Thr Val Val Glu Gly Glu Pro
 1               5                  10                  15
Phe Tyr Leu Lys His Cys Ser Cys Ser Leu Ala His Glu Ile Glu Thr
                 20                  25                  30
Thr Thr Lys Ser Trp Tyr Lys Ser Ser Gly Ser Gln Glu His Val Glu
             35                  40                  45
Leu Asn Pro Arg Ser Ser Arg Ile Ala Leu His Asp Cys Val Leu
         50                  55                  60
Glu Phe Trp Pro Val Glu Leu Asn Asp Thr Gly Ser Tyr Phe Phe Gln
 65                  70                  75                  80
Met Lys Asn Tyr Thr Gln Lys Trp Lys Leu Asn Val Ile Arg Arg Asn
                 85                  90                  95
Lys His Ser Cys Phe Thr Glu Arg
                100

(2) INFORMATION FOR SEQ ID NO: 25:

(i) SEQUENCE CHARACTERISTICS:
        (A) LENGTH: 307
        (B) TYPE: amino acid
        (D) TOPOLOGY: linear (ii) MOLECULE TYPE: peptide (xi) SEQUENCE DESCRIPTION: SEQ ID NO: 25:
```

```
Ser Lys Ser Cys Ile His Arg Ser Gln Ile His Val Glu Gly Glu
  1               5                  10                 15

Pro Phe Tyr Leu Lys Pro Cys Gly Ile Ser Ala Pro Val His Arg Asn
             20                  25                 30

Glu Thr Ala Thr Met Arg Trp Phe Lys Gly Ser Ala Ser His Glu Tyr
         35                  40                  45

Arg Glu Leu Asn Asn Arg Ser Ser Pro Arg Val Thr Phe His Asp His
     50                  55                  60

Thr Leu Glu Phe Trp Pro Val Glu Met Glu Asp Glu Gly Thr Tyr Ile
 65                  70                  75                  80

Ser Gln Val Gly Asn Asp Arg Arg Asn Trp Thr Leu Asn Val Thr Lys
                 85                  90                  95

Arg Asn Lys His Ser Cys Phe Ser Asp Lys Leu Val Thr Ser Arg Asp
            100                 105                 110

Val Glu Val Asn Lys Ser Leu His Ile Thr Cys Lys Asn Pro Asn Tyr
        115                 120                 125

Glu Glu Leu Ile Gln Asp Thr Trp Leu Tyr Lys Asn Cys Lys Glu Ile
    130                 135                 140

Ser Lys Thr Pro Arg Ile Leu Lys Asp Ala Glu Phe Gly Asp Glu Gly
145                 150                 155                 160

Tyr Tyr Ser Cys Val Phe Ser Val His His Asn Gly Thr Arg Tyr Asn
                165                 170                 175

Ile Thr Lys Thr Val Asn Ile Thr Val Ile Gly Arg Ser Lys Val
            180                 185                 190

Thr Pro Ala Ile Leu Gly Pro Lys Cys Glu Lys Val Gly Val Glu Leu
        195                 200                 205

Gly Lys Asp Val Glu Leu Asn Cys Ser Ala Ser Leu Asn Lys Asp Asp
    210                 215                 220

Leu Phe Tyr Trp Ser Ile Arg Lys Glu Asp Ser Asp Pro Asn Val
225                 230                 235                 240

Gln Glu Asp Arg Lys Glu Thr Thr Thr Trp Ile Ser Glu Gly Lys Leu
                245                 250                 255

His Ala Ser Lys Ile Leu Arg Phe Gln Lys Ile Thr Glu Asn Tyr Leu
            260                 265                 270

Asn Val Leu Tyr Asn Cys Thr Val Ala Asn Glu Glu Ala Ile Asp Thr
        275                 280                 285

Lys Ser Phe Val Leu Val Arg Lys Glu Ile Pro Asp Ile Pro Gly His
    290                 295                 300

Val Phe Thr
305

(2) INFORMATION FOR SEQ ID NO: 26:

(i) SEQUENCE CHARACTERISTICS:
        (A) LENGTH: 157
        (B) TYPE: amino acid
        (D) TOPOLOGY: linear (ii) MOLECULE TYPE: peptide (xi) SEQUENCE DESCRIPTION: SEQ ID NO: 26:

Tyr Phe Gly Lys Leu Glu Ser Lys Leu Ser Val Ile Arg Asn Leu Asn
  1               5                  10                 15

Asp Gln Val Leu Phe Ile Asp Gln Gly Asn Arg Pro Leu Phe Glu Asp
             20                  25                 30
```

```
Met Thr Asp Ser Asp Cys Arg Asp Asn Ala Pro Arg Thr Ile Phe Ile
            35                  40                  45

Ile Ser Met Tyr Lys Asp Ser Gln Pro Arg Gly Met Ala Val Thr Ile
 50                  55                  60

Ser Val Lys Cys Glu Lys Ile Ser Xaa Leu Ser Cys Glu Asn Lys Ile
 65                  70                  75                  80

Ile Ser Phe Lys Glu Met Asn Pro Pro Asp Asn Ile Lys Asp Thr Lys
                 85                  90                  95

Ser Asp Ile Ile Phe Phe Gln Arg Ser Val Pro Gly His Asp Asn Lys
                100                 105                 110

Met Gln Phe Glu Ser Ser Ser Tyr Glu Gly Tyr Phe Leu Ala Cys Glu
                115                 120                 125

Lys Glu Arg Asp Leu Phe Lys Leu Ile Leu Lys Lys Glu Asp Glu Leu
                130                 135                 140

Gly Asp Arg Ser Ile Met Phe Thr Val Gln Asn Glu Asp
145                 150                 155
```

(2) INFORMATION FOR SEQ ID NO: 27:

(i) SEQUENCE CHARACTERISTICS:
        (A) LENGTH: 157
        (B) TYPE: amino acid
        (D) TOPOLOGY: linear (ii) MOLECULE TYPE: peptide (xi) SEQUENCE DESCRIPTION: SEQ ID NO: 27:

```
Asn Phe Gly Arg Leu His Cys Thr Thr Ala Val Ile Arg Asn Ile Asn
 1                   5                  10                  15

Asp Gln Val Leu Phe Val Asp Lys Arg Gln Pro Val Phe Glu Asp Met
                 20                  25                  30

Thr Asp Ile Asp Gln Ser Ala Ser Glu Pro Gln Thr Arg Leu Ile Ile
            35                  40                  45

Tyr Met Tyr Lys Asp Ser Glu Val Arg Gly Leu Ala Val Thr Leu Ser
 50                  55                  60

Val Lys Asp Ser Lys Xaa Ser Thr Leu Ser Cys Lys Asn Lys Ile Ile
 65                  70                  75                  80

Ser Phe Glu Glu Met Asp Pro Pro Glu Asn Ile Asp Asp Ile Gln Ser
                 85                  90                  95

Asp Leu Ile Phe Phe Gln Lys Arg Val Pro Gly His Asn Lys Met Glu
                100                 105                 110

Phe Glu Ser Ser Leu Tyr Glu Gly His Phe Leu Ala Cys Gln Lys Glu
                115                 120                 125

Asp Asp Ala Phe Lys Leu Ile Leu Lys Lys Lys Asp Glu Asn Gly Asp
                130                 135                 140

Lys Ser Val Met Phe Thr Leu Thr Asn Leu His Gln Ser
145                 150                 155
```

(2) INFORMATION FOR SEQ ID NO: 28:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 28:

```
TCAGTCGACG CCACCATGAA TTGTAGAGAA                                   30

(2) INFORMATION FOR SEQ ID NO: 29:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 29:

GAAGCGGCCG CATCATTAAG ACTCGGAAAG AAC                               33

(2) INFORMATION FOR SEQ ID NO: 30:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 30:

TCAGTCGACG CCACCATGAA TTGTAGAGAA TTA                               33

(2) INFORMATION FOR SEQ ID NO: 31:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 31:

GAAGCGGCCG CATCATTATC TTGTGAAGAC GTG                               33

(2) INFORMATION FOR SEQ ID NO: 32:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 32:

TCAGTCGACG CCACCATGAA TTGTAGAG                                     28

(2) INFORMATION FOR SEQ ID NO: 33:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 33:

GAAGCGGCCG CTCATTAGTG ATGGTGATGG TGATGTGCAA CATGGTTAAG CCT         53

(2) INFORMATION FOR SEQ ID NO: 34:
```

(i) SEQUENCE CHARACTERISTICS:
    (A) LENGTH: 28 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 34:

TCAGTCGACG CCACCATGAA TTGTAGAG                28

(2) INFORMATION FOR SEQ ID NO: 35:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 35:

GAAGCGGCCG CTCATTAGTG ATGGTGATGG TGATGTCTTT CAGTGAAACA GCT           53

(2) INFORMATION FOR SEQ ID NO: 36:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 36:

TCAGTCGACG CCACCATGCA TCATGAAGAA              30

(2) INFORMATION FOR SEQ ID NO: 37:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 37:

GAAGCGGCCG CATCATTAGT GATGGTGATG GTGATGTGTA AAGACATGGC C            51